(12) United States Patent
Adachi et al.

(10) Patent No.: US 9,439,003 B2
(45) Date of Patent: Sep. 6, 2016

(54) UNCOMFORTABLE SOUND PRESSURE ESTIMATION SYSTEM, UNCOMFORTABLE SOUND PRESSURE ESTIMATION PROCESSOR, UNCOMFORTABLE SOUND PRESSURE ESTIMATION METHOD, AND COMPUTER PROGRAM THEREOF

(71) Applicant: Panasonic Intellectual Property Management Co., Ltd., Osaka (JP)

(72) Inventors: Shinobu Adachi, Nara (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 123 days.

(21) Appl. No.: 14/563,416

(22) Filed: Dec. 8, 2014

(65) Prior Publication Data

US 2015/0092949 A1 Apr. 2, 2015

Related U.S. Application Data

(63) Continuation of application No. PCT/JP2013/005871, filed on Oct. 2, 2013.

(30) Foreign Application Priority Data

Oct. 9, 2012 (JP) ................. 2012-223885

(51) Int. Cl.
*H04R 25/00* (2006.01)
*A61B 5/12* (2006.01)

(52) U.S. Cl.
CPC ................. *H04R 25/30* (2013.01); *A61B 5/12* (2013.01); *H04R 25/70* (2013.01)

(58) Field of Classification Search
None
See application file for complete search history.

(56) References Cited

U.S. PATENT DOCUMENTS

2006/0039576 A1* 2/2006 Roithinger ............. H04R 25/70
381/312
2009/0259277 A1* 10/2009 Cornejo Cruz .... A61B 5/04845
607/57

(Continued)

FOREIGN PATENT DOCUMENTS

JP 09-284898 A 10/1997
JP 2004-179965 A 6/2004

(Continued)

OTHER PUBLICATIONS

International Search Report for corresponding International Application No. PCT/JP2013/5871 dated Dec. 3, 2013.

(Continued)

*Primary Examiner* — Brenda Bernardi
(74) *Attorney, Agent, or Firm* — Renner, Otto, Boisselle & Sklar, LLP

(57) ABSTRACT

An exemplary uncomfortable sound pressure estimation system includes an HTL section for receiving information of hearing threshold levels respectively for a plurality of frequencies; a UCL measurement determination section for determining at least two measurement points at which to measure uncomfortable sound pressures, the at least two measurement points defining a first and a second frequency concerning a first and a second hearing threshold level; a UCL measurement section for measuring uncomfortable sound pressures with respect to the at least two measurement points; a calculation section for calculating a criterion concerning auditory characteristics by using the respective hearing threshold levels and uncomfortable sound pressures for the at least two points; and a UCL estimation section for estimating an uncomfortable sound pressure at a frequency corresponding to a given acquired hearing threshold level, according to the predetermined criterion.

16 Claims, 20 Drawing Sheets

(56) References Cited

U.S. PATENT DOCUMENTS

| | | | |
|---|---|---|---|
| 2010/0076338 A1* | 3/2010 | Kwak | A61B 5/04845 600/559 |
| 2012/0029383 A1* | 2/2012 | Henriksen | A61B 5/12 600/559 |
| 2012/0072213 A1* | 3/2012 | Adachi | A61B 5/04845 704/231 |
| 2013/0070929 A1 | 3/2013 | Adachi et al. | |
| 2013/0170661 A1* | 7/2013 | Sigwanz | H04R 25/70 381/60 |
| 2013/0182860 A1* | 7/2013 | Adachi | A61B 5/04845 381/60 |
| 2013/0266163 A1* | 10/2013 | Morikawa | A61B 5/04845 381/312 |
| 2013/0324880 A1* | 12/2013 | Adachi | A61B 5/7203 600/545 |
| 2014/0072127 A1 | 3/2014 | Adachi et al. | |
| 2015/0025808 A1* | 1/2015 | Aguiar | A61B 5/201 702/19 |

FOREIGN PATENT DOCUMENTS

| | | |
|---|---|---|
| JP | 2006-109083 A | 4/2006 |
| WO | WO 2012/063423 A1 | 5/2012 |
| WO | WO 2013/057929 A1 | 4/2013 |

OTHER PUBLICATIONS

Takashi Kimitsuki, et al., "Inner ear auditory testing in patients with normal hearing showing hyperacusis", Audiology Japan 52, pp. 152-156, 2009 and concise English explanation.

Shinobu Adachi et al., "Estimating uncomfortable loudness levels based on event-related potentials to triplets of auditory stimuli", Proceedings of the 51th Japanese Society for Medical and Biological Engineering, O1-10-1, 2012 and English abstract.

Jishoukanrendeni (ERP) Manyuaru—P300 WO Chushinni—(or "Event-Related Potential (ERP) Manual—mainly concerning P300-"), edited by Kimitaka Kaga et al., Shinohara Shuppan Shinsha, 1995; p. 30 and concise English explanation.

D.P. Pascoe, "Clinical measurements of the auditory dynamic range and their relation to formulas for hearing aid gain", in Iensen. H. I. (Ed.) Hearing Aid Fitting: Theoretical and Practical Views 13th Danavox Symposium. Copenhagen: Stougaard (1988).

Shinobu Adachi et al., Estimating Uncomfortable Loudness Levels Using Evoked Potentials to Auditory Stimuli for Hearing Aid Fitting, The Effect of Applied Sompressive Loading on Tissue-Engineered Cartilage Contructs Cultured With TGF-BETA3, IEEE, Aug. 28, 2012, pp. 2108-2111.

Extended European Search Report for corresponding European patent application No. 13845368.3, dated Sep. 14, 2015.

* cited by examiner

FIG. 4B
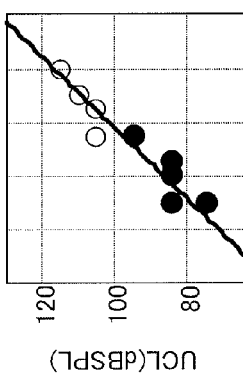
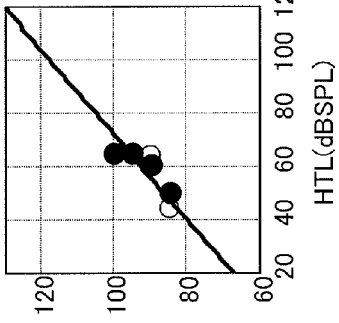
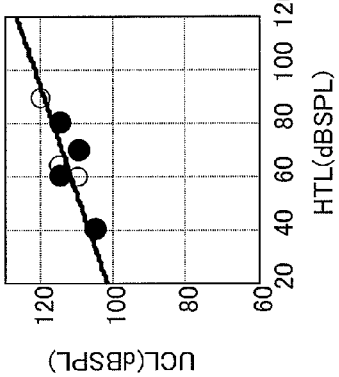
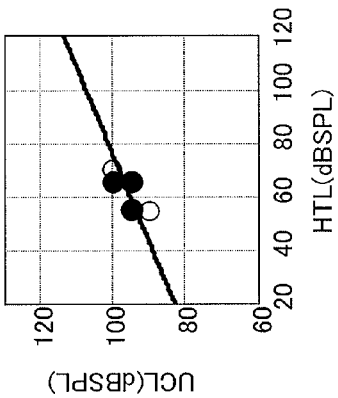
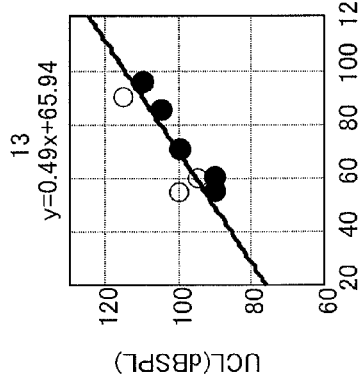
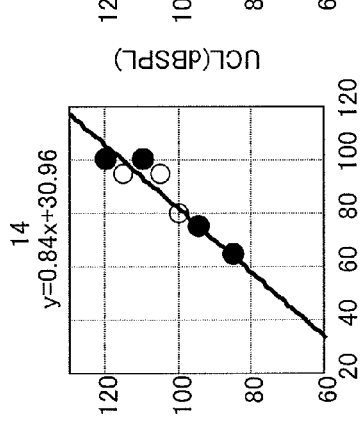
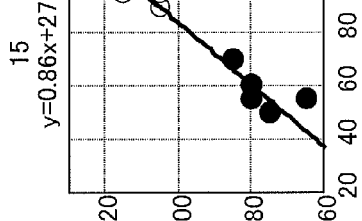
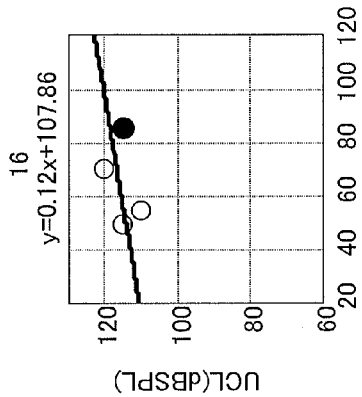

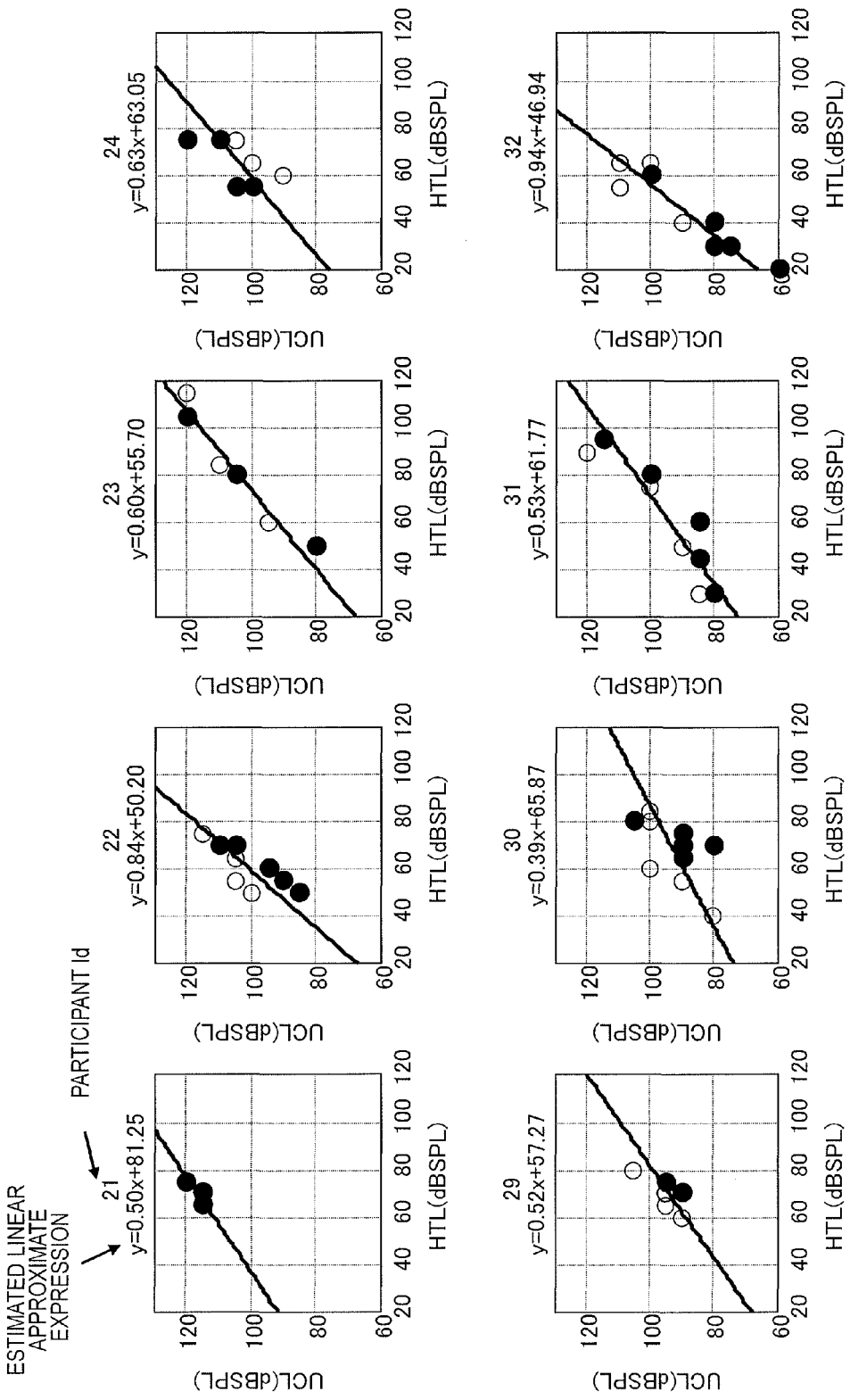

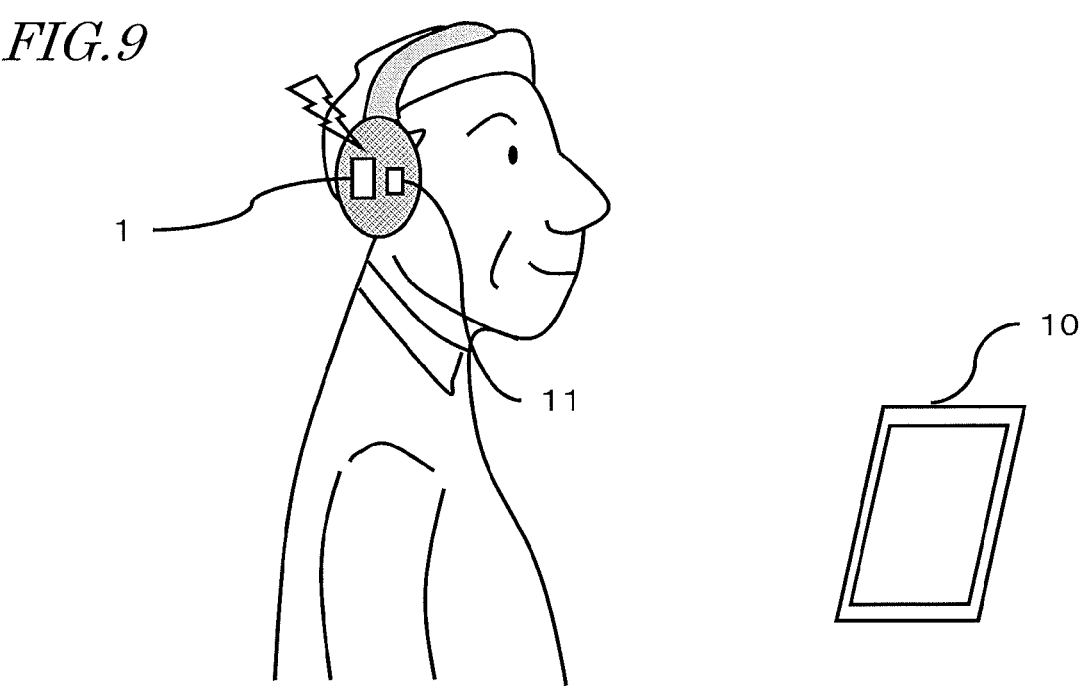

FIG.10

|  |  | HTL | UCL | |
| --- | --- | --- | --- | --- |
|  |  |  | MEASURED | ESTIMATED |
| RIGHT EAR | 250 Hz | 90 |  | 109.49 |
|  | 500 Hz | 90 |  | 109.49 |
|  | 1k Hz | 75 |  | 98.09 |
|  | 2k Hz | 85 |  | 105.69 |
|  | 4k Hz | 100 |  | 117.09 |
| LEFT EAR | 250 Hz | 65 | 85 | 90.49 |
|  | 500 Hz | 60 |  | 86.69 |
|  | 1k Hz | 50 | 75 | 79.09 |
|  | 2k Hz | 50 |  | 79.09 |
|  | 4k Hz | 75 | 95 | 98.09 |

UPPER VIEW    FRONT VIEW ions and Biological Engineering, O1-10-1, 2012 (Hereinafter, Non-Patent Document 2), discloses a technique of estimating a UCL of a person with normal hearing for each frequency, this technique using an auditory evoked potential in response to triplet sounds of 80 dBHL or less, which is not loud. Through the use of an electroencephalogram after having heard a sound stimulation of a non-loud sound pressure for a short time, a UCL estimation with a high precision is realized in a short time.

UNCOMFORTABLE SOUND PRESSURE ESTIMATION SYSTEM, UNCOMFORTABLE SOUND PRESSURE ESTIMATION PROCESSOR, UNCOMFORTABLE SOUND PRESSURE ESTIMATION METHOD, AND COMPUTER PROGRAM THEREOF

This is a continuation of International Application No. PCT/JP2013/005871, with an international filing date of Oct. 2, 2013, which claims priority of Japanese Patent Application No. 2012-223885, filed on Oct. 9, 2012, the contents of which are hereby incorporated by reference.

BACKGROUND

1. Technical Field

The present application relates to a technique of evaluating whether a sound has been heard in comfort. More specifically, the present disclosure relates to a system, processor, method, and computer program of estimating an uncomfortable sound pressure with respect to a sound, in the context of "fitting" of a hearing aid or the like, i.e., adjusting an amount of amplification for each frequency of an external sound to arrive at a sound of a loudness which is appropriate to each individual user.

2. Description of the Related Art

In recent years, people who are suffering from hypacusia because of old age that need hearing aids are increasing. Their number is said to be about 20 million domestically, and about 500 million globally (as investigated by the Japan Hearing Instruments Manufacturers Association). Before beginning use of a hearing aid, "fitting" is required for adjusting the amount of sound amplification for each frequency in accordance with the auditory characteristics of the user. It is generally difficult to complete fitting in one timeg1, and the user needs to visit a hearing aid shop several times to make readjustments. One reason thereof is that an uncomfortable sound pressure (uncomfortable loudness level: UCL) cannot be correctly measured. A UCL is often determined through calculation from a hearing threshold level (HTL) because a test based on subjective reporting would require loud sounds to be made, which leads to psychological stress and fatigue. However, there is a problem in that a calculated UCL which will not reflect individual differences.

"Inner ear auditory testing in patients with normal hearing showing hyperacusis", Takashi KIMITSUKI et al., Audiology Japan, 2009, Vol. 52, P. 152-156 (Hereinafter, Non-Patent Document 1), discloses a method of actually measuring a UCL through subjective report. A UCL which is actually measured through subjective report may hereinafter be referred to as a subjective UCL. A subjective UCL is obtained by, using an audiometer, presenting a continuous sound to a user by ascending method (i.e., gradually increasing the sound pressure level), and asking the user to report whether it is at a sound pressure that is too loud to be heard for a long time. The sound pressure which is reported by the user is defined as the subjective UCL. "Subjective reporting" involves, after a user hears a sound, the user making a subjective account as to how the sound was felt to him or her.

Moreover, techniques for estimating UCL by using an electroencephalogram, which reflects electrical activities of the brain, are being developed in the recent years. "Estimating uncomfortable loudness levels based on event-related potentials to triplets of auditory stimuli", Shinobu ADACHI et al., Proceedings of the 51th Japanese Society for Medical

SUMMARY

The methods disclosed in Non-Patent Document 1 and Non-Patent Document 2 could measure UCL only with respect to the ear and frequency for which actual measurements were taken through subjective reporting or sound stimulations were presented in order to estimate UCL based on electroencephalogram. Therefore, enormous test time was needed to specifically determine a UCL for every frequency which permits adjustment in a hearing aid.

One non-limiting, and exemplary embodiment of the present application provides an uncomfortable sound pressure estimation system which is able to estimate a UCL for each frequency in a relatively simple manner and with a good accuracy.

In one general aspect, an uncomfortable sound pressure estimation system according to an embodiment of the present invention includes: an HTL acquisition section configured to acquire information of hearing threshold levels respectively for a plurality of frequencies; a UCL measurement point determination section configured to determine at least two measurement points at which to measure uncomfortable sound pressures, each of the at least two measurement points at least defining a first frequency concerning a first hearing threshold level and a second frequency concerning a second hearing threshold level among the acquired hearing threshold levels, the second hearing threshold level being of a different level from the first hearing threshold level; a UCL measurement section configured to measure uncomfortable sound pressures with respect to the at least two determined measurement points; a calculation section configured to calculate a predetermined criterion concerning auditory characteristics by using the respective hearing threshold levels and uncomfortable sound pressures for the at least two measurement points determined by the UCL measurement point determination section; and a UCL estimation section configured to estimate an uncomfortable sound pressure at a frequency corresponding to a given hearing threshold level acquired by the HTL acquisition section, according to the predetermined criterion.

According to the above aspect, by taking UCL measurements with respect to at least two measurement points with different HTLs, UCLs with respect to other measurement points for which only HTL measurements were taken can be estimated with a high precision. Therefore, through a hearing aid adjustment which is based on the result of estimation, a hearing aid fitting is realized that does not allow the user to feel loudness.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 4B is a diagram showing exemplary HTL-UCL distributions and linear approximation lines of different participants in an auditory characteristics measurement experiment conducted by the inventors.

FIG. 4D is a diagram showing exemplary HTL-UCL distributions and linear approximation lines of different participants in an auditory characteristics measurement experiment conducted by the inventors.

FIG. 9 is a diagram showing an environment of use for an uncomfortable sound pressure estimation system.

FIG. 10 is a diagram showing an example of result accumulation in a result accumulating DB.

DETAILED DESCRIPTION

Figure 1:
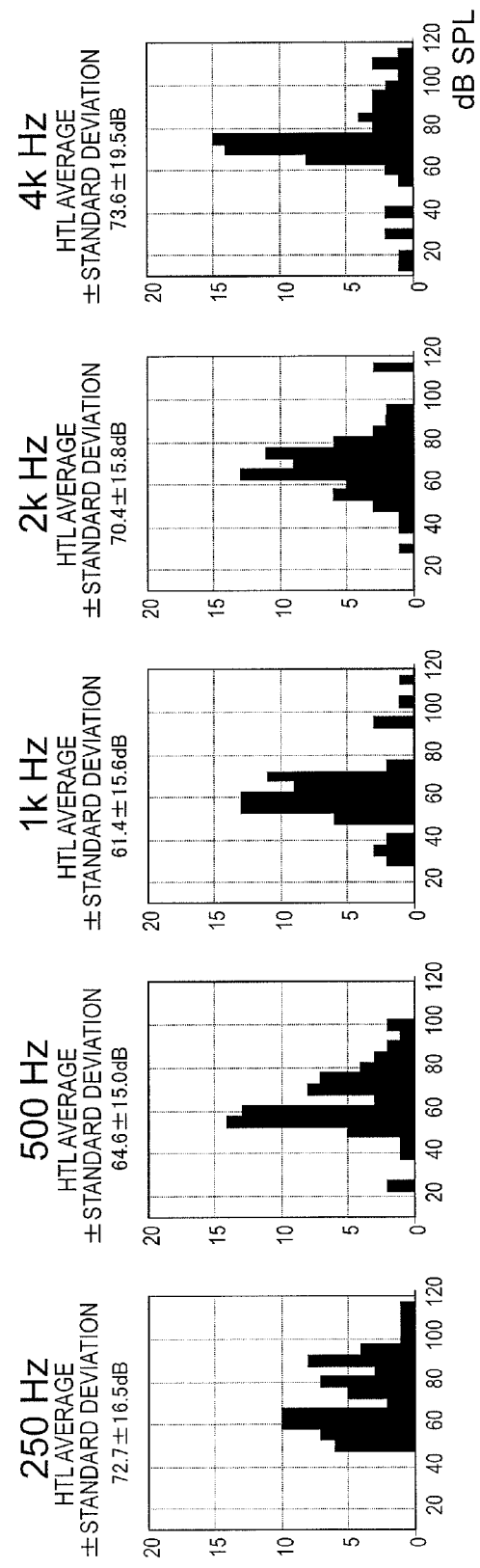
FIG. 1 is a diagram showing exemplary histograms of HTL measurement results in an auditory characteristics measurement experiment conducted by the inventors.

First, the definitions of the terms used in the present specification will be described.

An "uncomfortable sound pressure (uncomfortable loudness level: UCL)" is the largest sound pressure which a user can keep hearing for a long time without feeling uncomfortable.

An "auditory threshold value or a hearing threshold level (HTL)" is the sound pressure of a softest sound is audible to a user.

A "measurement point for auditory characteristics" is a point at which to examine auditory characteristics concerning UCL, HTL, and so on, which is defined by either the right or left ear and by sound frequency (e.g., 1 kHz on the right ear) in the case where auditory characteristics of both right and left ears are to be measured. It may be defined only by sound frequency when either the right or left ear is to be examined. It may simply be referred to as a "measurement point".

An "event-related potential (even-related potential: ERP)" is a fluctuation in the potential of an electroencephalogram (electroencephalogram: EEG) that occurs in connection with a certain stimulation.

An "N1 component" is a negative potential which is induced in a time range of not less than 50 ms and not more than 150 ms since the point of presenting a sound stimulation, in an event-related potential.

A "P2 component" is a positive potential which is induced in a time range of not less than 150 ms and not more than 250 ms since the point of presenting a sound stimulation, in an event-related potential.

A "sound stimulation" is a sound which is presented to a user. To "present a sound" means to output a pure tone.

A "pure tone" is a sound which repetitively undergoes periodic oscillation at a single frequency, such that it is expressed as a sine wave.

"Latency" is the time, based on the point of presenting a sound stimulation as a starting point, until a peak potential of a positive component or a negative component appears. As used herein, a peak potential means a peak potential that takes a local maximum or a local minimum in the time slot.

In the present specification, in order to define a component of an event-related potential, a point in time after the lapse of a predetermined time since a given point is expressed as a "latency of about 100 ms", for example. This means possible inclusion of a range around the specific point of 100 ms.

In the present specification, in order to define a component of an event-related potential, a point in time after the lapse of a predetermined time since a given point is expressed by referring to a "latency of about 100 ms", for example. This means possible inclusion of a range around the specific point of 100 ms. Generally speaking, there are 30 to 50 ms of differences (shifts) in event-related potential waveform between individuals, according to table 1 on p. 30 of "JISHOUKANRENDENI (ERP) MANYUARU-P300 WO CHUSHINNI- (or "Event-Related Potential (ERP) Manual-mainly concerning P300-"), edited by Kimitaka KAGA et al., Shinohara Shuppan Shinsha, 1995)". Therefore, in the present specification, "about X ms" and "near X ms" are interpreted as inclusive of a breadth of 30 to 50 ms before or after X ms (e.g., 100 ms±30 ms, 200 ms±50 ms).

A "negative component" generally refers to a potential which is smaller than 0 μV. A "positive component" generally refers to a potential which is greater than 0 μV. However, in a comparison between two potentials, the potential having the more negative value may be referred to as a negative component. Similarly, in a comparison between two potentials, the potential having the more positive value may be referred to as a positive component.

Hereinafter, with reference to the attached drawings, embodiments of the uncomfortable sound pressure estimation system will be described.

By taking UCL measurements with respect to at least two measurement points with different HTLs, an uncomfortable sound pressure estimation system according to an embodiment of the present invention makes high-precision UCL estimations, including other measurement points for which only HTL measurements were taken. The present invention relies on the correspondence between HTLs and UCLs of each person suffering from hypacusia which was found through an experiment which the inventors conducted for people suffering from hypacusia. Prior to describing the embodiments of the present invention, experiments conducted by the inventors, and the experimental results, will be described in detail. Moreover, a method of UCL estimation by linear approximation devised by the inventors will be described. Thereafter, embodiments of the uncomfortable sound pressure estimation system will be described in outline, together with their constructions and operations.

(Description of Experimental Outline)

1. Experimental Outline

The inventors have examined auditory characteristics of people suffering from hypacusia concerning HTL and UCL. Specifically, through subjective reporting, HTL and UCL were measured of people suffering from hypacusia who were about to begin use of a hearing aid.

It was consequently found that people suffering from hypacusia have large individual differences in UCL, which makes it impossible to rely on a common criterion to determine UCLs of all users.

When determining a UCL from an HTL through calculation, it is usual practice to calculate, from an HTL for each measurement point, a UCL for that measurement point. This is because it was conventionally believed that the UCLs for different measurement points were independent, there being no correlation with the HTL and UCLs of dissimilar measurement points (e.g., the opposite ear or different frequencies). However, through vigorous research, the inventors have found that characteristics of each individual person suffering from hypacusia manifest themselves in the relationship between HTL and UCL, even across different measurement points. Specifically, a linear relationship was found to exist between the HTL and the UCL of each individual person, irrespective of the right or left ear and the sound frequency.

Based on this finding, it was confirmed that, by actually measuring UCLs with respect to at least two measurement points with different HTLs, and obtaining an approximate expression (regression line) that represents the relationship between HTLs and UCLs by a least-squares method, for example, it is possible to estimate UCL values with respect to measurement points on the ear not selected for UCL measurement or measurement points at frequencies not selected for UCL measurement, with a high precision from HTL values.

(Description of Experimental Method)

For 34 people suffering from hypacusia who were about to begin use of a hearing aid (17 males, 17 females, 27 to 88 years old, average 71.9 years old), an experiment of measuring auditory characteristics concerning HTL and UCL was conducted. Informed consent was obtained for participating in the experiment.

HTL and UCL were measured by using an SPL audiometer (D2-36H, manufactured by DANA JAPAN). The measurement points were: 250 Hz on the right ear, 500 Hz on the right ear, 1 kHz on the right ear, 2 kHz on the right ear, 4 kHz on the right ear, 250 Hz on the left ear, 500 Hz on the left ear, 1 kHz on the left ear, 2 kHz on the left ear, and 4 kHz on the left ear. A HTL and a UCL were measured for each measurement point.

The upper limit of the output sound pressure of the SPL audiometer was 120 dBSPL. Continuous sounds (continuing sounds without disruptions or pauses) were used as the sound stimulations. First, HTL was measured, and then UCL was measured.

While consecutively increasing or consecutively decreasing the sound pressure of sound stimulations, HTL was measured for each measurement point. It was asked that a hand be raised while the sound was being heard, and the smallest sound pressure at which the sound began to be heard was recorded as the HTL for each measurement point. UCL was measured for each measurement point by ascending method. It was asked that a hand be raised when it was too loud to hear, and this was recorded as the UCL for each measurement point.

Hereinafter, results of the experiment will be discussed. Any instance where HTL or UCL was not measurable in a range equal to or less than 120 dBSPL, which is the upper limit output sound pressure of the SPL audiometer, was excluded from the analysis.

FIG. 1 shows frequency-by-frequency histograms of HTL across all participants. The histograms shown in FIG. 1 include measurement results for the left ear and the right ear of the participants.

The average values±standard deviations of HTL were 72.7±16.5 dBSPL, 64.6±15.0 dBSPL, 61.4±15.6 dBSPL, 70.4±15.8 dBSPL, and 73.6±19.5 dBSPL at 250 Hz, 500 Hz, 1 kHz, 2 kHz, and 4 kHz, respectively.

Figure 2:
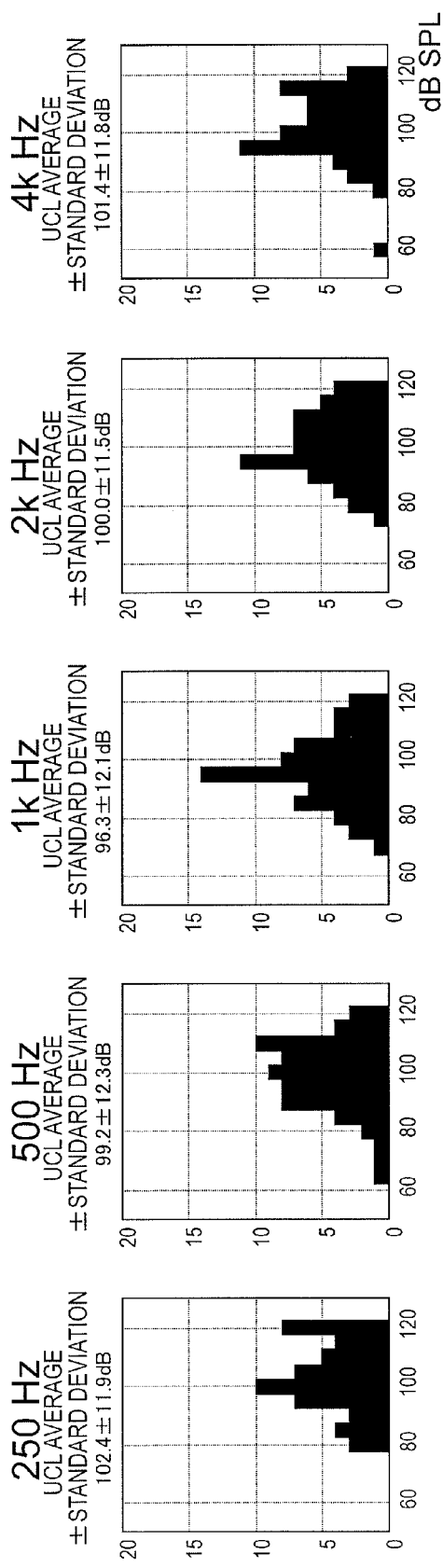
FIG. 2 is a diagram showing exemplary histograms of UCL measurement results in an auditory characteristics measurement experiment conducted by the inventors.

FIG. 2 shows frequency-by-frequency histograms of UCL across all participants. The histograms shown in FIG. 2 include measurement results for the left ear and the right ear of the participants. The average values±standard deviations of UCL were 102.4±11.9 dBSPL, 99.2±12.3 dBSPL, 96.3±12.1 dBSPL, 100.0±11.5 dBSPL, and 101.4±11.8 dBSPL at 250 Hz, 500 Hz, 1 kHz, 2 kHz, and 4 kHz, respectively.

Figure 3:
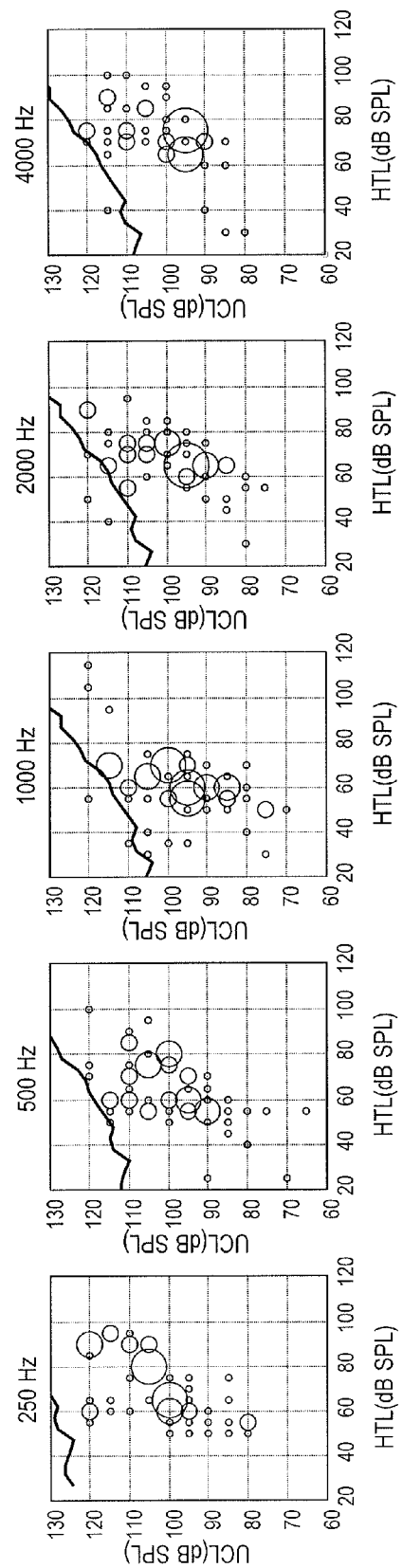
FIG. 3 is a diagram showing exemplary HTL-UCL distributions in an auditory characteristics measurement experiment conducted by the inventors.

FIG. 3 shows, with circles, distributions of HTL and UCL measurement results for different frequencies. The distributions shown in FIG. 3 include measurement results for the left ear and the right ear of the participants. The horizontal axis represents HTL, and the vertical axis represents UCL, both in units of dBSPL. From the left, results at 250 Hz, 500 Hz, 1 kHz, 2 kHz, and 4 kHz are respectively shown. At each lattice point, occurrence frequency is indicated by a circle in a corresponding size.

It can be seen from FIG. 3 that the UCL value greatly fluctuates for the same HTL value, especially when the HTL is equal to or less than 80 dBSPL. The maximum value of difference in UCL value for the same frequency and the same HTL value was 50 dB. This indicates that the sound pressure which is felt "unbearably loud" greatly differs for each individual person, and that it is difficult to estimate a UCL from an HTL through some universal calculation.

Together with HTL and UCL measurement results, FIG. 3 also shows UCL values for different HTLs reported in Pascoe, D. P. (1988), (Clinical measurements of the auditory dynamic range and their relation to formulas for hearing aid gain. In Jensen. H. 1. (Ed.) Hearing Aid Fitting: Theoretical and Practical Views 13th Danavox Symposium. Copenhagen: Stougaard.), these being converted into the dBSPL unit and shown by bold lines. From the relationship between the bold line and the circles, it can be seen that the UCL values of most participants are smaller than the UCL values which are reported in the conventional study. These taken together, it is considered difficult to determine UCLs of all participants from HTLs based on a common criterion.

The inventors have paid attention to the relationship between HTL and UCL as measured in units of dBSPL for each participant. They have thus found that, within the bounds of each participant, linear approximation of HTL-UCL relationship is possible across different measurement points (right or left ear and frequency). This finding indicates that, by measuring UCL with respect to two or more measurement points with different HTLs (e.g., 1 kHz on the right ear and 2 kHz on the left ear), it is possible to estimate UCL with respect to other measurement points for which only HTL measurements were taken (e.g., 250, 500, 2 k, 4 kHz on the right ear and 250, 500, 1 k, 4 kHz on the left ear). This finding allows to reduce the number of measurement points that present a burden to the user in UCL measurement. For example, in the case where HTL differs between the right and left ears, measuring UCL on the ear having a lesser degree of hypacusia makes it possible to estimate UCL, from an HTL, without measuring UCL on the ear having more serious hypacusia.

Figure 4A:
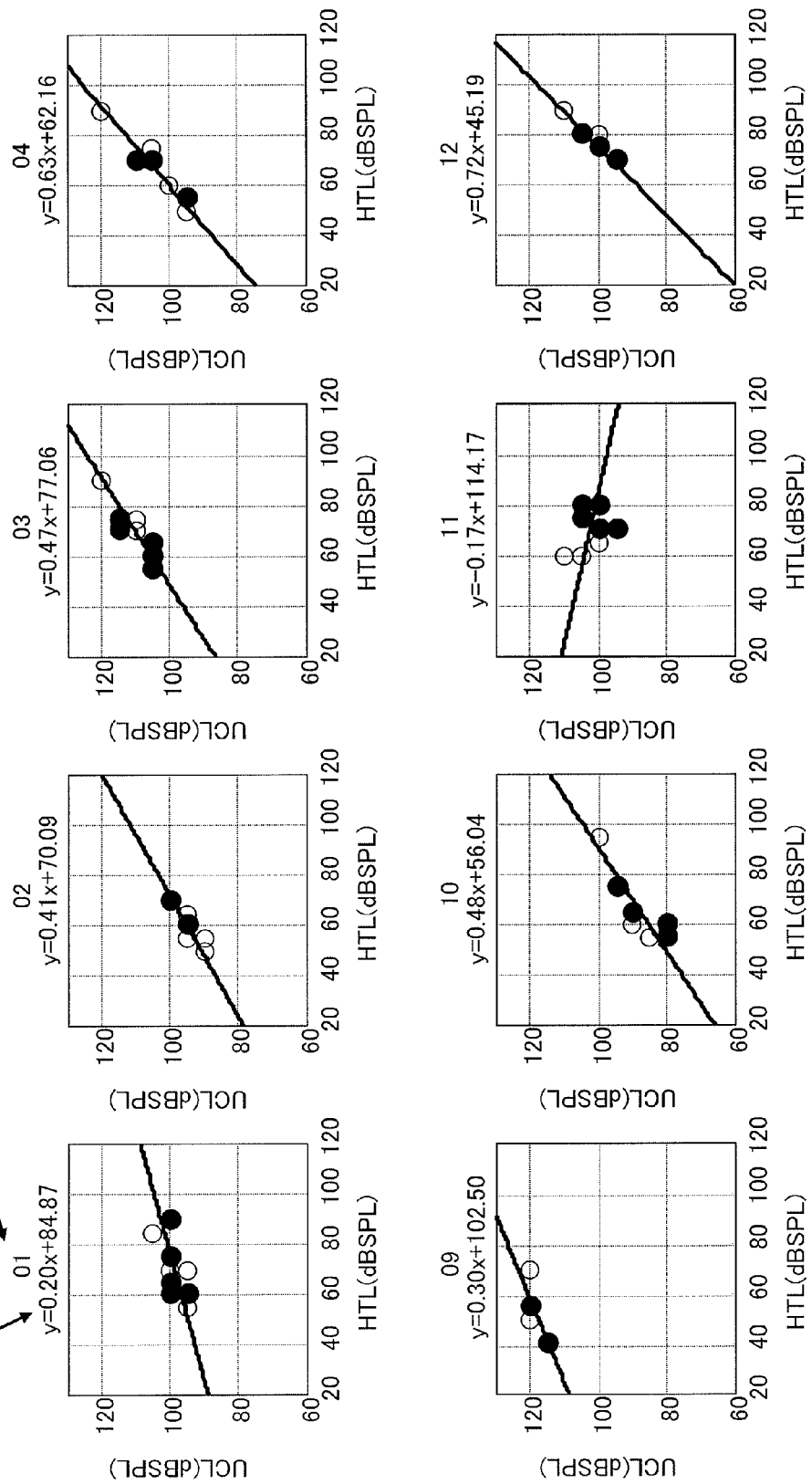
FIG. 4A is a diagram showing exemplary HTL-UCL distributions and linear approximation lines of different participants in an auditory characteristics measurement experiment conducted by the inventors.
Figure 4C:
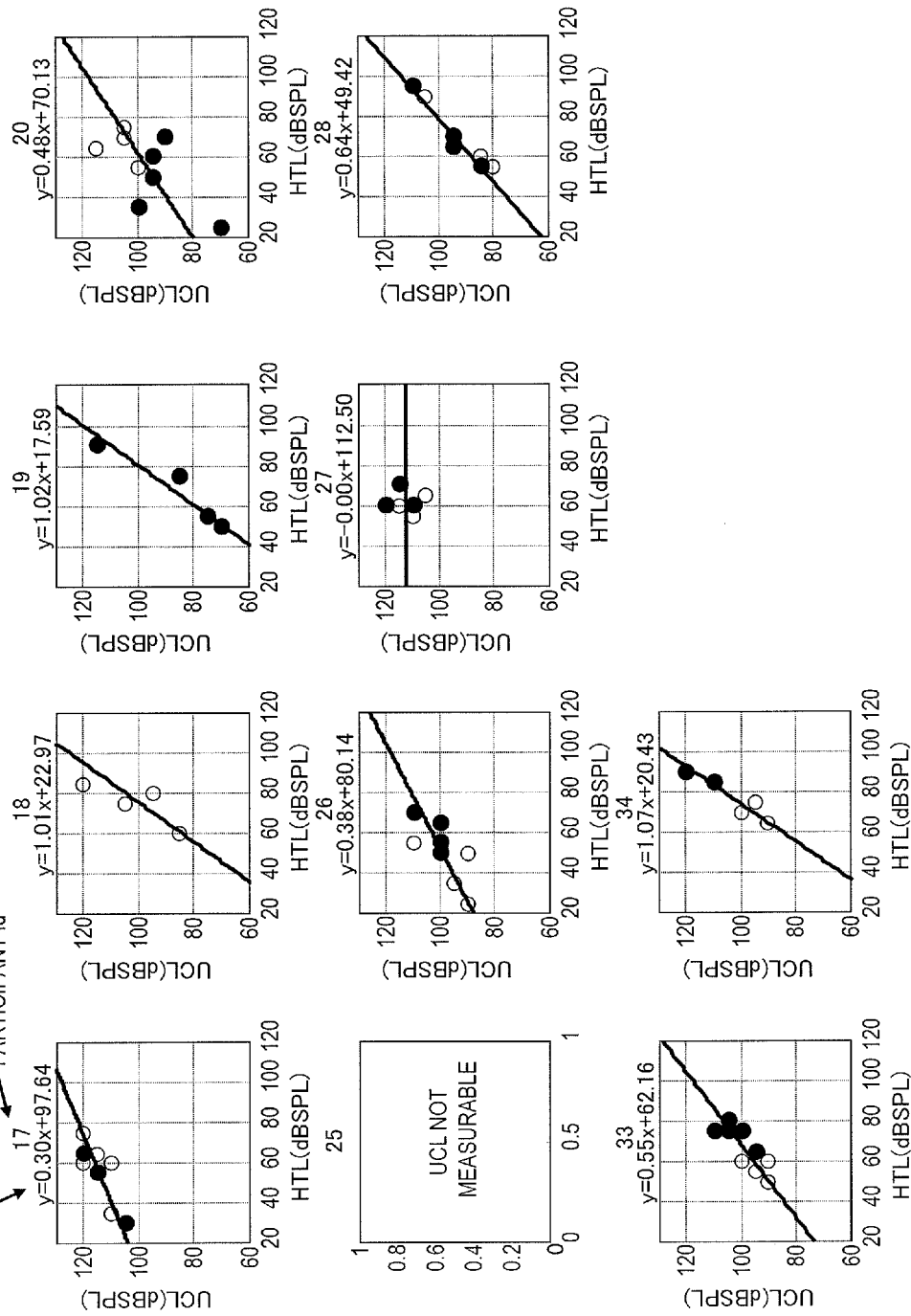
FIG. 4C is a diagram showing exemplary HTL-UCL distributions and linear approximation lines of different participants in an auditory characteristics measurement experiment conducted by the inventors.

FIG. 4A to FIG. 4D show HTL-UCL distributions of different participants for all measurement points at which HTL and UCL were measurable (i.e., being equal to or less than 120 dBSPL) in the auditory characteristics measurement experiment by the inventors. Similarly to FIG. 3, the horizontal axis represents HTL and the vertical axis represents UCL, both in units of dBSPL. Results for the right ear are indicated with white circles, and results for the left ear are indicated with black circles. In each graph, a linear approximation line that approximates HTL and UCL is shown. The linear approximation line was obtained for each participant by least-squares method, using the measurement values of successfully measured HTL and UCL. It can be seen from FIG. 4A to FIG. 4D that the HTL and UCL for each measurement point are well approximated by the linear approximation. For example, although Participant 05 and Participant 15 FIG. 4B show significantly differing hearing for the right and left ears, these are still well approximated. This indicates that, once an HTL value for each measurement point and the gradient and intercept of the linear approximation line are known, it is possible to estimate the UCL based on the HTL value.

Figure 5:
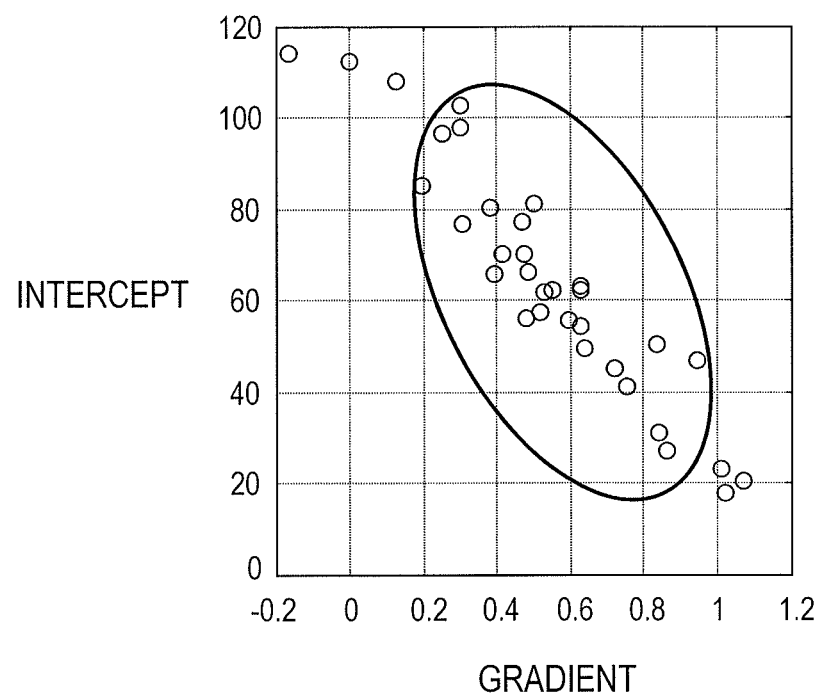
FIG. 5 is a diagram showing an exemplary gradient-intercept distribution of linear approximation lines in an auditory characteristics measurement experiment conducted by the inventors.

FIG. 5 shows a gradient-intercept distribution of linear approximation lines from different participants. In 80% or more of the participants, the gradient was not less than 0.2 and not more than 1, and the intercept was not less than 20 dBSPL and not more than 100 dBSPL. As for Participant 25 (FIG. 4C), UCL was not measurable in any measurement point.

Figure 6:
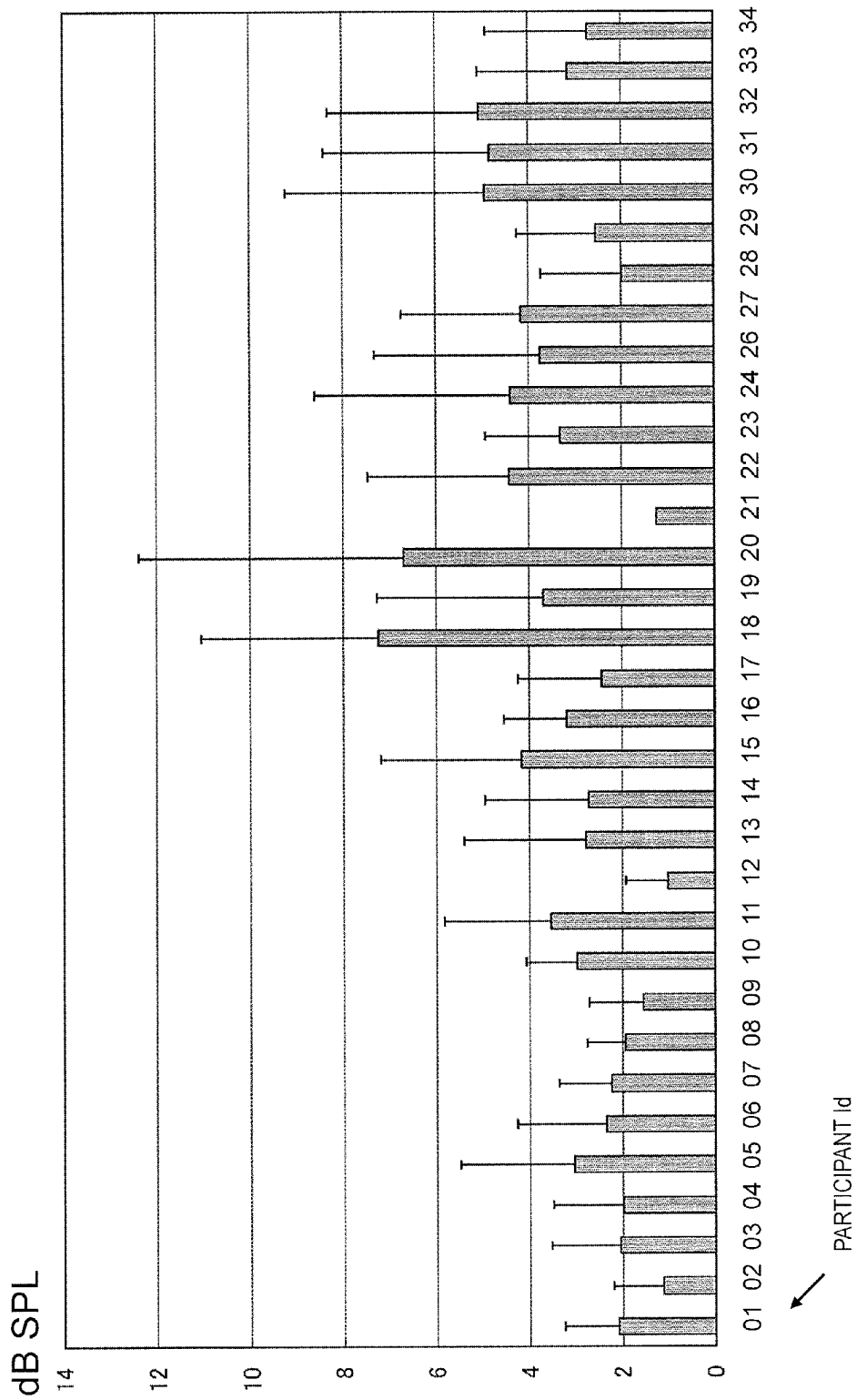
FIG. 6 is a diagram showing exemplary errors between actually-measured UCLs and UCLs determined through linear approximation of different participants.

FIG. 6 shows mean errors between actually-measured UCLs and estimated UCLs, which were estimated from a linear approximation line and the HTL value for each measurement point, of different participants. The overall mean error was 3.20 dBSPL. Considering that the smallest graduation of an audiometer is 5 dB, it can be said that linear approximation allows UCLs to be estimated with a high precision.

Figure 7:
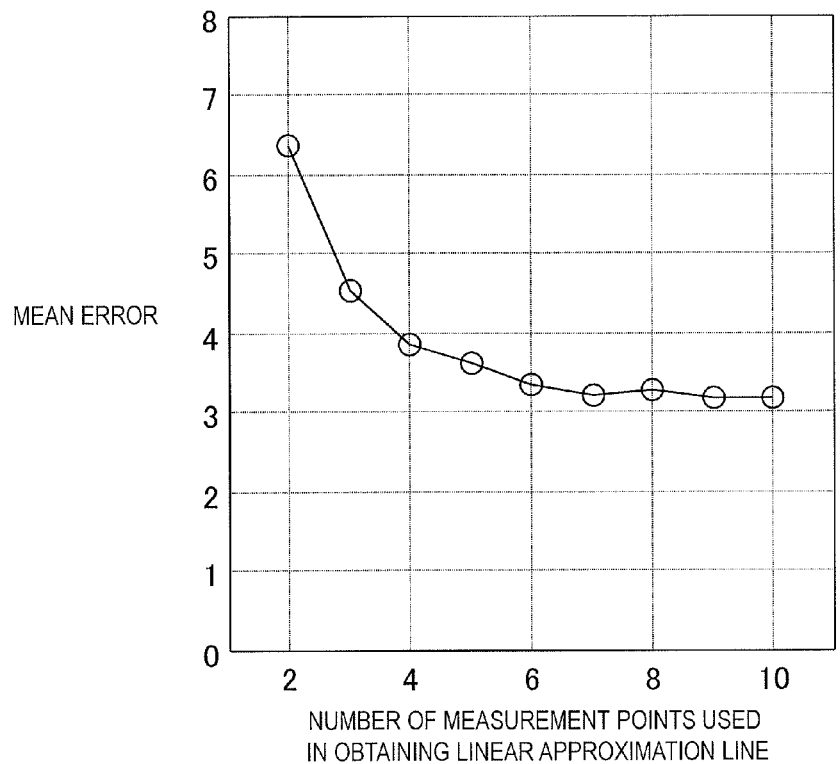
FIG. 7 is a diagram showing exemplary numbers of measurement points use when determining a linear approximation line and exemplary mean errors for different numbers of measurement points.

FIG. 7 shows a relationship between the number of measurement points used when determining a linear approximation line and mean estimation errors for different number of measurement points. In FIG. 7, the horizontal axis represents the number of measurement points used when determining a linear approximation line, and the vertical axis represents a mean error for each number of measurement points. The mean error for each number of measurement points was obtained by, for each given number of measurement points: extracting a combination of measurement points that would result in two or more HTL values; calculating a linear approximation line for each combination, and estimating a UCL for every measurement point; and performing averaging to derive a mean error with respect to actually-measured UCLs. It can be said from FIG. 7 that, even when the number of measurement points is two, the mean estimation error is 7 dB or less, thus enabling UCL estimation with a certain degree of accuracy. It can also be seen that, while the number of measurement points is six or less, the mean error decreases as the number of measurement points increases, but while number of measurement points is greater than six, there is not much difference in mean error.

Thus, the experiment conducted by the inventors has indicated that a proportional relationship (a relationship that permits linear approximation) exists between the HTL and UCL of each person suffering from hypacusia, irrespective of the measurement point. It has also been found that, by using UCL values actually measured with respect to at least two measurement points with different HTLs, UCLs with respect to other measurement points for which only HTL measurements were taken can be estimated from an approximate expression. Specifically, HTLs are measured in advance with respect to measurement points at which UCL is to be determined, and, from among them, two measurement points with different HTL values are selected. Actual measurements of UCL are taken only at the selected measurement points to derive a linear approximation line. Substituting an HTL from any other measurement point allows UCL estimation, including those measurement points at which UCL was not measured. As a result, a hearing aid fitting that does not allow the user to feel loudness can be easily realized.

Embodiment 1

Hereinafter, first, the uncomfortable sound pressure estimation system will be described in outline. Thereafter, a construction and operation for an uncomfortable sound pressure estimation system which includes the uncomfortable sound pressure estimation apparatus will be described.

Figure 8A:
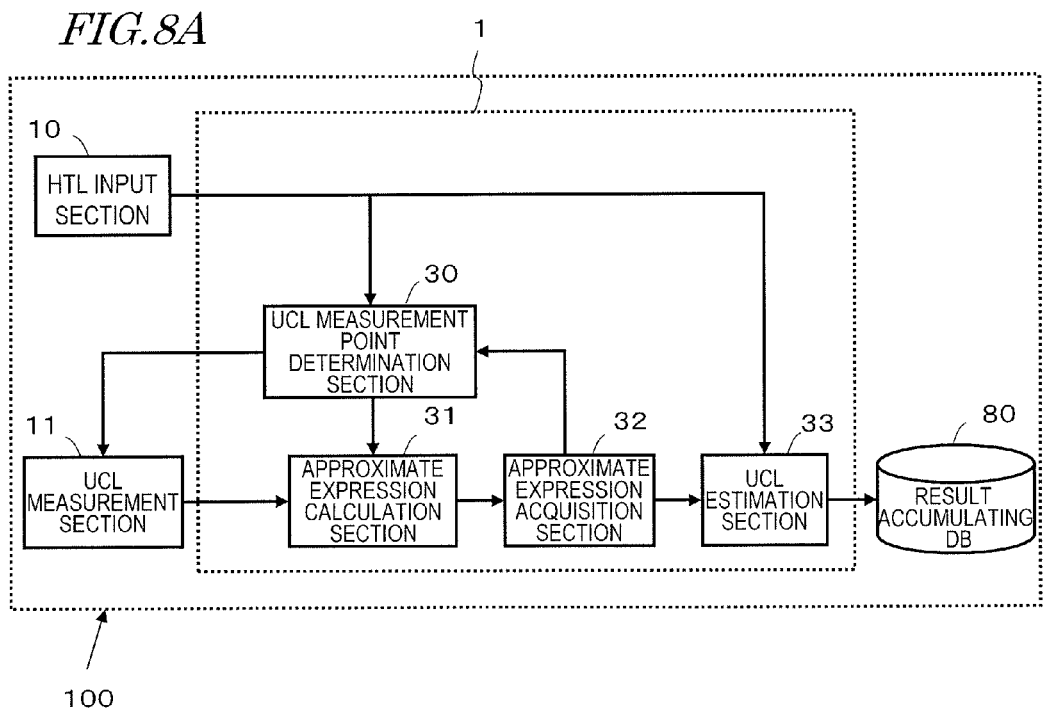
FIG. 8A is a diagram showing the construction of an implementation of an uncomfortable sound pressure estimation system according to Embodiment 1.

FIG. 8A shows the functional block construction of an uncomfortable sound pressure estimation system 100 according to the present embodiment. The uncomfortable sound pressure estimation system 100 includes an HTL input section 10, a UCL measurement section 11, an uncomfortable sound pressure estimation apparatus 1, and a result accumulating DB 80.

The uncomfortable sound pressure estimation apparatus 1 shown in FIG. 8A includes a UCL measurement point determination section 30, an approximate expression calculation section 31, an approximate expression acquisition section 32, and a UCL estimation section 33. The uncomfortable sound pressure estimation apparatus 1 may at least include the UCL measurement point determination section 30, the approximate expression calculation section 31, and the UCL estimation section 33.

The uncomfortable sound pressure estimation apparatus 1 is connected in a wired or wireless manner to the HTL input section 10, the UCL measurement section 11, and the result accumulating DB 80 for exchange of information.

<Environment of Use>

FIG. 9 shows a construction and an environment of use for the uncomfortable sound pressure estimation system according to the present embodiment. The uncomfortable sound pressure estimation system shown in FIG. 9 corresponds to the system construction of the uncomfortable sound pressure estimation system 100 of Embodiment 1 shown in FIG. 8A.

The uncomfortable sound pressure estimation system includes the uncomfortable sound pressure estimation apparatus 1, the HTL input section 10, and the UCL measurement section 11.

The uncomfortable sound pressure estimation apparatus 1 and the UCL measurement section 11 shown in FIG. 9 are accommodated in one housing. The uncomfortable sound pressure estimation apparatus 1 is wirelessly connected to the HTL input section 10 for exchange of information. The HTL input section 10 may be implemented by application software which is executed on a tablet terminal, for example. Moreover, the result accumulating DB 80 may be an accumulation in a storage device which is included in such a terminal.

A user inputs an HTL for each measurement point to the HTL input section 10. The HTL input section 10 receives the input HTL, and sends it to the uncomfortable sound pressure estimation apparatus 1. By using a relationship between the HTLs which are input to the HTL input section 10 and the UCLs measured by the UCL measurement section 11, the uncomfortable sound pressure estimation apparatus 1 calculates a predetermined criterion. Furthermore, by referring to the predetermined criterion, the uncomfortable sound pressure estimation apparatus 1 estimates a UCL using an HTL which is input to the HTL input section 10. Thus, by using the predetermined criterion representing the relationship between HTLs and UCLs (reference equation), which is derived from actually-measured HTLs and UCLs, the uncomfortable sound pressure estimation apparatus 1 of the present embodiment estimates a UCL with respect to a measurement point at which only the HTL was measured. Hereinafter, the respective component elements will be described.

<HTL Input Section 10>

For each measurement point, the HTL input section 10 accepts the user's input of an HTL. For example, HTLs for the left ear and the right ear and for different sound frequencies, measured in advance, are input.

HTL is information which is associated with the left ear or the right ear of the user, and sound frequency, for example. In the case where of measuring the auditory characteristics of only one ear, the HTL may be information which is associated with a sound frequency. IL is desirable that the HTL is in units of dBSPL.

Measurement points according to the present embodiment may be, for example, 250 Hz on the right ear, 500 Hz on the right ear, 1 kHz on the right ear, 2 kHz on the right ear, 4 kHz on the right ear, 250 Hz on the left ear, 500 Hz on the left ear, 1 kHz on the left ear, 2 kHz on the left ear, and 4 kHz on the left ear. Alternatively, they may be all frequencies that permit adjustment on a hearing aid. Although it is assumed that HTL is to be measured for every measurement point in principle, it may be determined in a complementary manner from HTL values for close frequencies. For example, by setting 1.5 kHz as a measurement point, an average value between the actually-measured HTLs for 1 kHz and 2 kHz on the right ear may be utilized as an HTL for 1.5 Hz. Such variants are encompassed within the present invention.

<UCL Measurement Point Determination Section 30>

The UCL measurement point determination section 30 receives an HTL of the user for each measurement point from the HTL input section 10. Among the received HTLs, the UCL measurement point determination section 30 selects a plurality of HTLs of different values, and determines UCL measurement points (i.e., measurement points at which to actually measure UCLs) corresponding to the selected plurality of HTLs. The UCL measurement point determination section 30 sends information of the determined UCL measurement points to the UCL measurement section 11. Moreover, the UCL measurement point determination section 30 sends the HTLs with respect to the determined measurement points to the approximate expression calculation section 31.

As the measurement points to actually measure UCL, a plurality of measurement points need to be selected that will result in two or more HTL values. In other words, it should not be the case that the HTLs for the plurality of measurement points to actually measure UCL, as determined by the UCL measurement point determination section 30, all have the same value.

When the HTLs for different measurement points received from the HTL input section 10 have three or more values, the measurement points may be prioritized in a predetermined manner so that the measurement points will be consecutively selected in descending order of priority. Specifically, higher priority may be assigned for measurement points of frequencies close to 1 kHz, which is considered important for conversational hearing (e.g., frequencies in a range not less than 0.9 kHz and not more than 1.1 kHz).

With such selection, a hearing aid fitting using actually-measured UCL values can be realized at least for measurement points with high priority. Moreover, for example, two measurement points with a great difference in HTL may be chosen from among the HTLs for different measurement points having been input, while excluding any outliers not belonging to the predetermined sound pressure range. This makes it possible to reduce errors in the gradient and intercept of the linear approximation line, thereby improving the accuracy of UCL estimation.

Moreover, in the case where the degree of hypacusia differs between the right and left ears by a predetermined difference or more (e.g., there being an HTL difference of 20 dBSPL or more between the right and left ears), UCL measurement points may be selected from the ear with a lighter degree of hypacusia (i.e., smaller HTL values) first. From the results of Participant 05 and Participant 15 shown in FIG. 4B, it can be said that UCL values on the ear with the lesser degree of hypacusia are often smaller than the UCLs on the ear with the greater degree of hypacusia. By thus selecting the better-hearing ear for the measurement points to actually measure UCL, it becomes possible to estimate UCL for both ears, including the hypacusia ear, in such a manner that the user will not hear any loud sound during the actual measurement of UCL.

Thus, based on the HTLs for the right and left ears and for different frequencies received from the HTL input section 10, for example, the UCL measurement point determination section 30 is able to determine two or more measurement points at which to actually measure UCLs, and measurement points at which to derive UCL through estimation without involving actual measurement. The UCL estimation section 33, described later, is able to estimate a UCL at a measurement point for which measurement was not taken by the UCL measurement section 11.

<UCL Measurement Section 11>

The UCL measurement section 11 measures UCL at the determined measurement points. For UCL measurement, sound stimulations related to the determined measurement points are output to the user from an output section which is included in the UCL measurement section 11, these sound stimulations being in a predetermined sound pressure range, for example. The sound stimulations may be continuous sounds (continuing sounds without disruptions or pauses), or discontinuous sounds (i.e., disrupted sounds, such as 500 ms of presentation and then a 500 ms pause). Moreover, sound stimulations may be output by an ascending method, such that the sounds increase in sound pressure in a stepwise manner. The measured UCLs are sent to the uncomfortable sound pressure estimation apparatus 1.

<Approximate Expression Calculation Section 31>

Based on the HTLs for different measurement points received from the UCL measurement point determination section 30 and the UCLs for different measurement points received from the UCL measurement section 11, the approximate expression calculation section 31 calculates a predetermined criterion concerning auditory characteristics of HTL and UCL with respect to each given user. In the present embodiment, the predetermined criterion is information of a proportional relationship between HTLs and UCLs. Specifically, it is a proportional relationship between the amount of change in UCL relative to the difference between HTLs for measurement points. For example, as shown in FIG. 4A to FIG. 4D, it may be a linear function (an equation whose degree of variables is one) that defines a proportional relationship between HTLs and UCLs. Note that the predetermined criterion does not need to be coefficients of a linear function, but may be a polynomial which is substantially capable of linear approximation.

One example of the predetermined criterion is an approximate expression which linearly approximates the HTL-UCL distribution. Calculation of the approximate expression may be performed by a least-squares method, for example. To the approximate expression acquisition section 32, the approximate expression calculation section 31 sends the determined predetermined criterion (e.g., the approximate expression or coefficients (gradient and intercept)) of the approximate expression).

<Approximate Expression Acquisition Section 32>

The approximate expression acquisition section 32 acquires the predetermined criterion which has been calculated by the approximate expression calculation section 31.

Figure 8B:
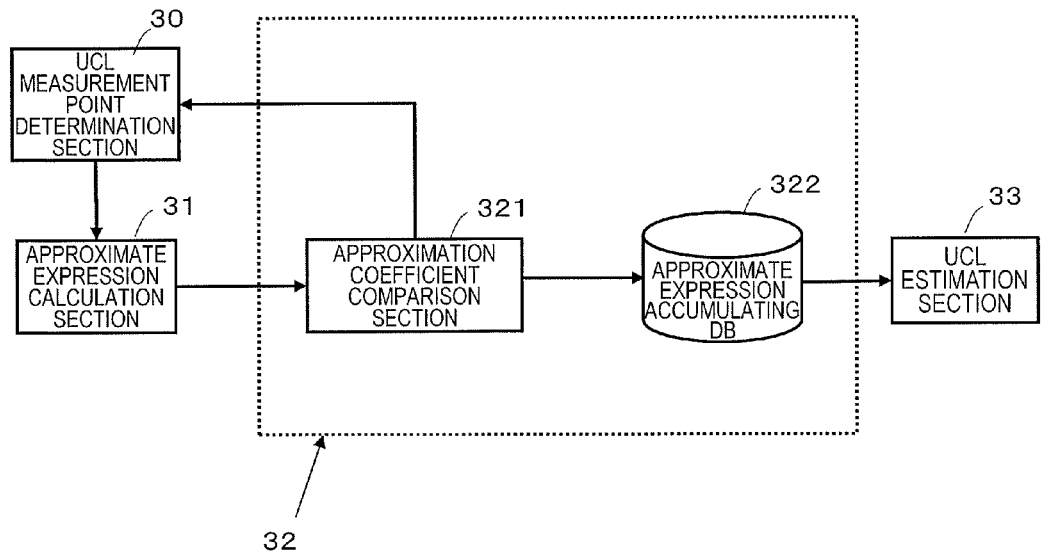
FIG. 8B is a diagram showing the construction of an implementation of an uncomfortable sound pressure estimation system according to Embodiment 1.

As shown in FIG. 8B, the approximate expression acquisition section 32 may include an approximation coefficient comparison section 321 and an approximate expression accumulating DB 322. In this case, as the predetermined criterion, the approximation coefficient comparison section 321 acquires the coefficients of the approximate expression, and compares the acquired coefficients of the approximate expression against predetermined ranges which are stored in advance, for example.

If the coefficients of the approximate expression lie outside the predetermined ranges, the approximation coefficient comparison section 321 may send that information to the UCL measurement point determination section 30; and if the coefficients of the approximate expression are within the predetermined ranges, the approximation coefficient comparison section 321 may send the coefficients of the approximate expression to the UCL estimation section 33. The predetermined ranges may be, for example, the gradient of the approximate expression being not less than 0.2 and not more than 1, and the intercept being not less than 20 dBSPL and not more than 100 dBSPL. From the approximation coefficient comparison section 321, the UCL measurement point determination section 30 receives information as to whether the coefficients of the approximate expression lie outside the predetermined ranges, and if they do, at least one measurement point to actually measure UCL according to the aforementioned criterion is added.

For example, the approximate expression calculation section 31 calculates an approximate expression by using UCLs for the newly-added measurement point(s), and the UCLs for the initially-determined measurement points. Alternatively, the approximate expression calculation section 31 calculates an approximate expression by using UCLs for the newly-added plural measurement points. The approximation coefficient comparison section 321 accumulates the predetermined criterion in the approximate expression accumulating DB 322. Note that the approximate expression acquisition section 32 may merely send to the UCL estimation section 33 the predetermined criterion which is calculated by the approximate expression calculation section 31. In this case, the approximate expression acquisition section 32 may be omitted.

<UCL Estimation Section 33>

The UCL estimation section 33 receives HTLs for different measurement points from the HTL input section 10, and receives UCL values at measurement points for which UCLs were actually measured, and the predetermined criterion, from the approximate expression acquisition section 32. An example of the predetermined criterion is a gradient and an intercept of an approximate expression.

By referring to the predetermined criterion, the UCL estimation section 33 estimates a UCL for each measurement point received from the HTL input section 10. For example, the UCL estimation section 33 substitutes an HTL value for each measurement point into the approximate expression to derive a UCL for that measurement point. The derived UCL for each measurement point is sent to the result accumulating DB 80. As for any measurement point for which a UCL was actually measured, both the actually-measured UCL received from the approximate expression acquisition section 32 and the UCL estimated from the approximate expression may be sent. The former and the latter will have different values when three or more measurement points are selected in the UCL measurement point determination section 30.

Moreover, the UCL estimation section 33 may be adapted so as to correct a UCL estimated from the approximate expression based on an actually-measured UCL. For example, in order to use an actually-measured UCL for any frequency near 1 kHz, which is considered important for conversational hearing, the intercept of the approximate expression may be corrected so that the difference between the estimated UCL and the actually-measured UCL at that frequency is zero, thus allowing the value of the estimated UCL for each measurement point to be corrected.

<Result Accumulating DB 80>

The result accumulating DB 80 accumulates the HTL and UCL for each measurement point received from the UCL estimation section 33. Examples of accumulated information may be the HTL and UCL for each measurement point that is determined in terms of the right or left ear and frequency. FIG. 10 is an example of data accumulation in the result accumulating DB 80. This exemplifies a case where an HTL and an actually-measured value and an estimated value of UCL are to be accumulate for each measurement point. Given the same HTL value (e.g., 75 dB for 1 kHz on the right ear and 75 dB for 4 kHz on the left ear in FIG. 10), the estimate UCL values are the same (98.09 dB).

<Processing by the Uncomfortable Sound Pressure Estimation System 100>

Figure 11A:
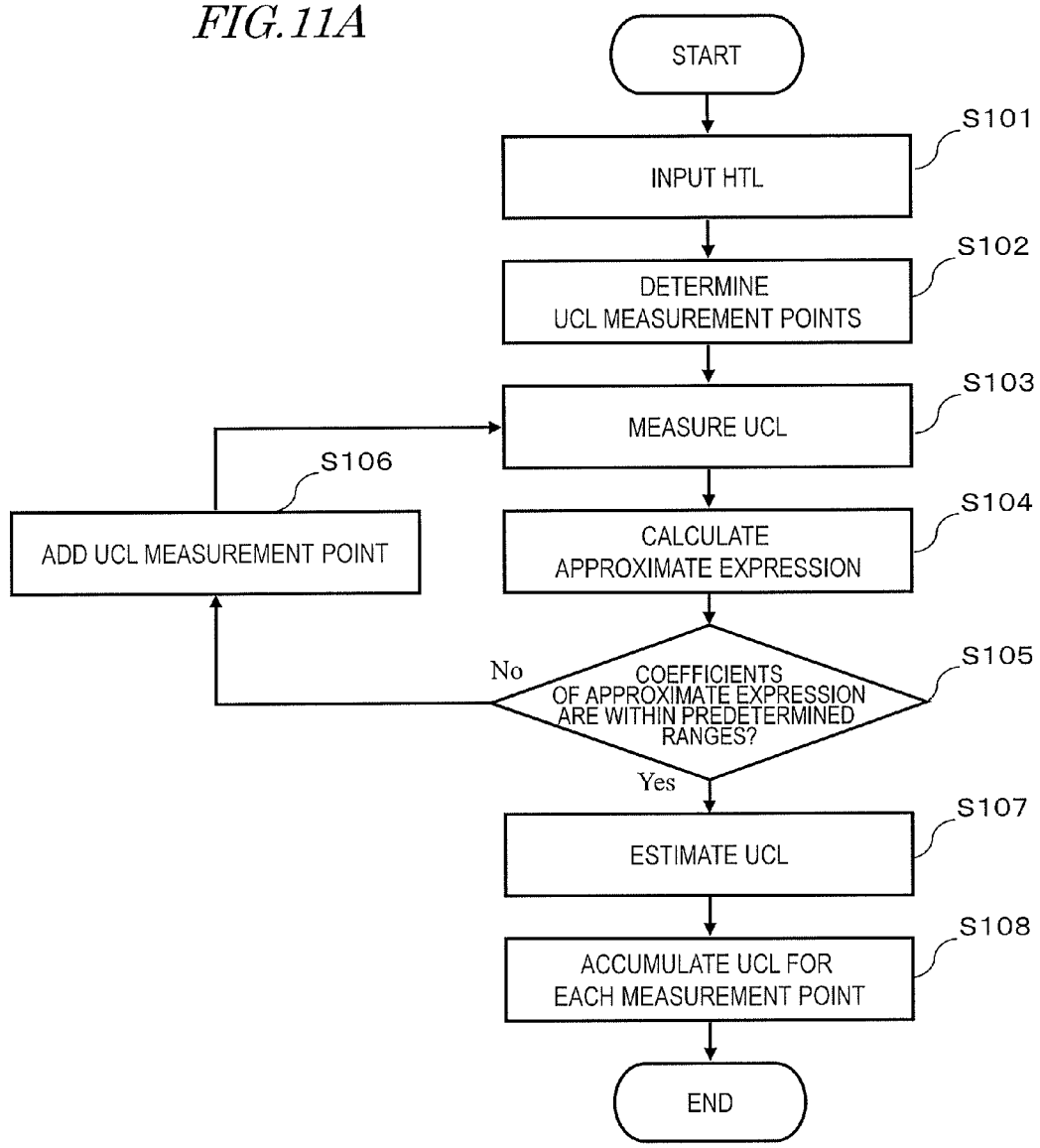
FIG. 11A is a flowchart showing an overall processing by the uncomfortable sound pressure estimation system in outline.

Next, with reference to FIG. 11A, a processing procedure of the uncomfortable sound pressure estimation system 100 in FIG. 8A will be described. FIG. 11A is a flowchart showing a procedure of processing by the uncomfortable sound pressure estimation system 100.

<step S101> The HTL input section 10 accepts an HTL of the user which has been actually measured for each measurement point. The input HTL is associated with each measurement point differing in terms of sound frequency or the right or left ear. For example, it is an HTL in units of dBSPL, for each of the left ear or right ear of the user and for each frequency, that has been measured in advance. Among the accepted HTLs for different measurement points, at least HTLs of different values are included. The HTL input section 10 sends information of the accepted HTLs to the UCL measurement point determination section 30. A "measurement point" is information at least including sound frequency, and may include the user's left ear or right ear as well as sound frequency.

<step S102> The UCL measurement point determination section 30 receives an HTL for each measurement point of the user from the HTL input section 10. From among the received HTLs, the UCL measurement point determination section 30 determines two or more measurement points of different HTL values, and sends them to the UCL measurement section 11. Moreover, the UCL measurement point determination section 30 sends the HTLs with respect to the determined measurement points to the approximate expression calculation section 31.

<step S103> The UCL measurement section 11 measures UCL at the measurement points determined by the UCL measurement point determination section 30. The UCL measurement section 11 measures a sound pressure which is felt too loud for the user to keep hearing any more as the UCL. Moreover, it sends the actually-measured UCL for each measurement point to the approximate expression calculation section 31.

Figure 11B:
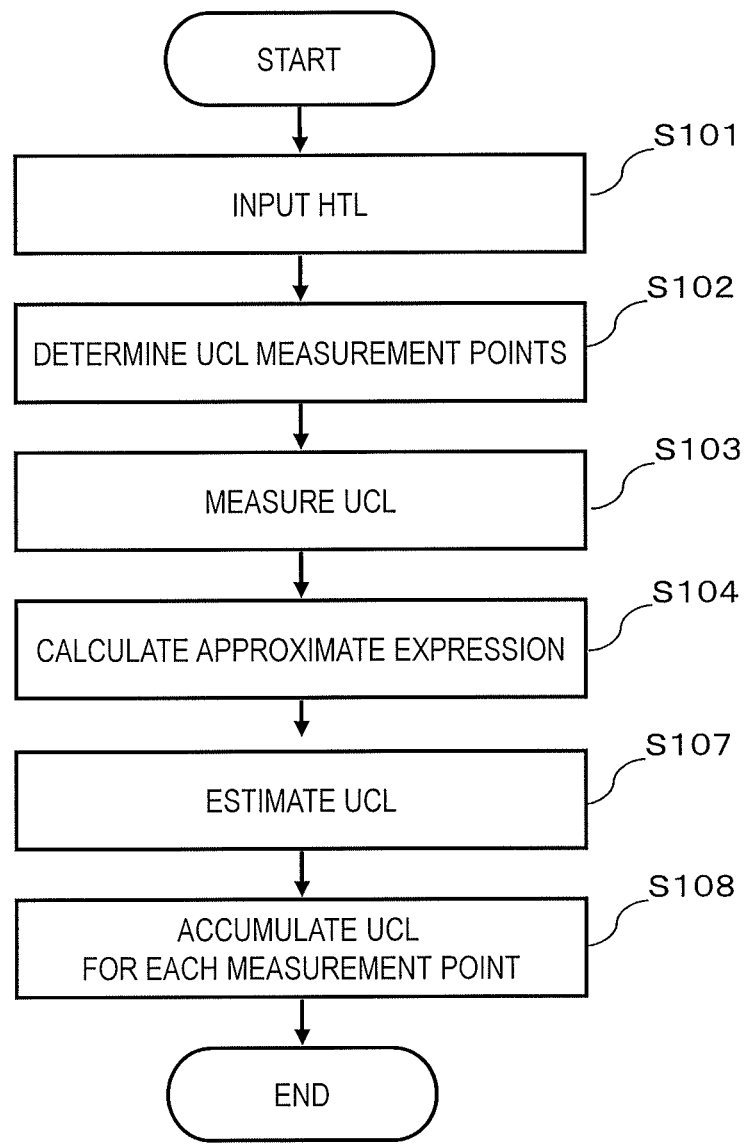
FIG. 11B is a flowchart showing an overall processing by the uncomfortable sound pressure estimation system in outline.
Figure 11C:
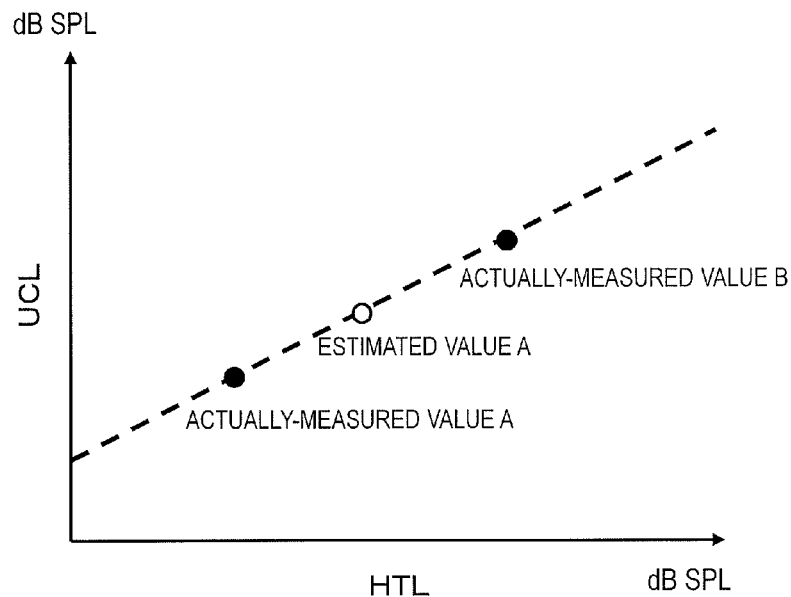
FIG. 11C is a diagram illustrating uncomfortable sound pressure estimation in outline.

<step S104> The approximate expression calculation section 31 accepts the HTL for each measurement point as received from the UCL measurement point determination section 30, and the UCL for each measurement point as received from the UCL measurement section 11. Based on the received HTL values and UCL values, the approximate expression calculation section 31 calculates an approximate expression which linear approximates the HTL-UCL distribution. An approximate expression through linear approximation is an example of the predetermined criterion. FIG. 11C shows an exemplary approximate expression. In FIG. 11C, the vertical axis represents UCL, and the horizontal axis represents HTL. HTL values corresponding to actually-measured value A and actually-measured value B are received from the UCL measurement point determination section 30, and UCL values corresponding to actually-measured value A and actually-measured value B are received from the UCL measurement section 11. Based on the received HTL value and UCL value, the approximate expression calculation section 31 calculates an approximate expression as indicated by a dotted line in FIG. 11C.

Calculation of the approximate expression may be performed by a least-squares method, for example. The approximate expression calculation section 31 sends the calculated coefficients of the approximate expression to the approximate expression acquisition section 32.

<step S105> The approximation coefficient comparison section 321 included in the approximate expression acquisition section 32 determines whether the coefficients of the approximate expression received from the approximate expression calculation section 31 are within the predetermined ranges of values stored in advance or not.

If the coefficients of the approximate expression lie outside the predetermined ranges (No from step S105), control proceeds to step S106, and the UCL measurement point determination section 30 is instructed to add a measurement point at which to actually measure UCL.

If the coefficients of the approximate expression are within the predetermined ranges (Yes from step S105), control proceeds to step S107, and the approximate expression having coefficients falling within the predetermined ranges are accumulated in the approximate expression accumulating DB 322 included in the approximate expression acquisition section 32. The predetermined ranges may be, for example, the gradient of the approximate expression being not less than 0.2 and not more than 1, and the intercept being not less than 20 dBSPL and not more than 100 dBSPL.

<step S106> The approximation coefficient comparison section 321 included in the approximate expression acquisition section 32 informs the UCL measurement point determination section 30 that the coefficients of the approximate expression lie outside the predetermined ranges. As an additional UCL measurement point, the UCL measurement point determination section 30 determines a measurement point which is different from the measurement points for UCL determined at step S102.

Note that the UCL measurement point determination section 30 may determine the same measurement point as a measurement point determined at S102. Generally, UCL measurement values are likely to fluctuate. When a value is not within the previously-retained predetermined range, the UCL measurement point determination section 30 may determine the same measurement point as a measurement point determined at S102, so that UCL is again actually measured at the same measurement point.

<step S107> The UCL estimation section 33 receives an HTL for each measurement point from the HTL input section 10, and receives coefficients concerning the gradient and intercept of the approximate expression, from the approximate expression accumulating DB 322 included in the approximate expression acquisition section 32. Then, the HTL for each measurement point received from the HTL input section 10 is substituted in the approximate expression to derive a respective UCL.

Specifically, the HTL for estimated value A as shown in FIG. 11C is accepted, and, by using information of the proportional relationship between HTLs and UCLs (approximate expression) shown by the dotted line, a UCL for estimated value A is estimated. For example, a UCL for an HTL different from the HTL which was used when determining information of the proportional relationship between HTLs and UCLs is estimated.

The HTL and UCL for each measurement point are sent to the result accumulating DB 80. As for any measurement point for which a UCL was actually measured, both the actually-measured UCL and the UCL derived from the approximate expression may be sent. The former and the latter will have different values when three or more measurement points are selected in the UCL measurement point determination section 30.

<step S108> The result accumulating DB 80 stores the UCL values for the UCL estimation section 33 in a measurement point-by-measurement point manner.

With the uncomfortable sound pressure estimation system 100 of the present embodiment, by taking UCL measurements with respect to at least two measurement points with different HTLs, whereby UCL or other measurement points can be estimated with a high precision. As a result, a hearing aid fitting is realized during which the number of times that the user feels loudness is reduced.

<Hardware Construction of Uncomfortable Sound Pressure Estimation Apparatus 1>

Figure 15:
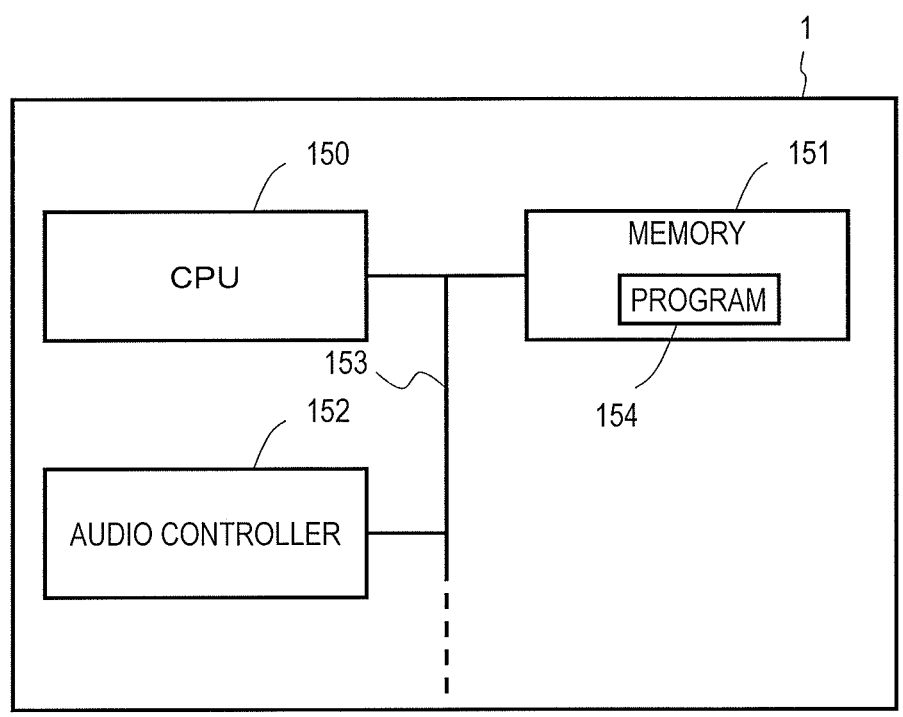
FIG. 15 is a diagram showing the hardware construction of Embodiment 1 and Embodiment 2.

FIG. 15 shows an exemplary hardware construction of the uncomfortable sound pressure estimation apparatus 1 according to the present embodiment.

The uncomfortable sound pressure estimation apparatus 1 includes a CPU 150, a memory 151, and an audio controller 152. The CPU 150, the memory 151, and the audio controller 152 are interconnected via a bus 153, so that data exchange among them is possible.

The CPU 150 executes a computer program 154 which is stored in the memory 151. A processing procedure as illustrated by the aforementioned flowchart is described in the computer program 154. In accordance with the computer program 154, the uncomfortable sound pressure estimation apparatus 1 performs processes to control the entire uncomfortable sound pressure estimation system 100, e.g., generation of sound stimulations, calculation of an approximate expression, and UCL estimation.

In accordance with instructions from the CPU 150, the audio controller 152 outputs each sound stimulation to be presented via a sound stimulation output section (e.g., headphones or a loudspeaker) at a designated sound pressure.

Note that the uncomfortable sound pressure estimation apparatus 1 may be implemented as a piece of hardware (e.g., a DSP) consisting of a semiconductor circuit having a computer program incorporated therein. Such a DSP can realize all functions of the aforementioned CPU 150, memory 151, and audio controller 152 on a single integrated circuit.

The aforementioned computer program 154 may be distributed on the market in the form of a product recorded on a storage medium such as a CD-ROM, or transmitted through telecommunication lines such as the Internet. Upon reading the computer program 154, a device having the hardware shown in FIG. 15 (e.g., a PC) is able to function as the uncomfortable sound pressure estimation apparatus 1 according to the present embodiment.

The respective functional blocks of the uncomfortable sound pressure estimation apparatus 1 correspond to functions which are realized by the CPU 150, the memory 151, and the audio controller 152 as a whole upon executing the program which has been described in conjunction with FIG. 15.

Variant 1 of Embodiment 1

Figure 8C:
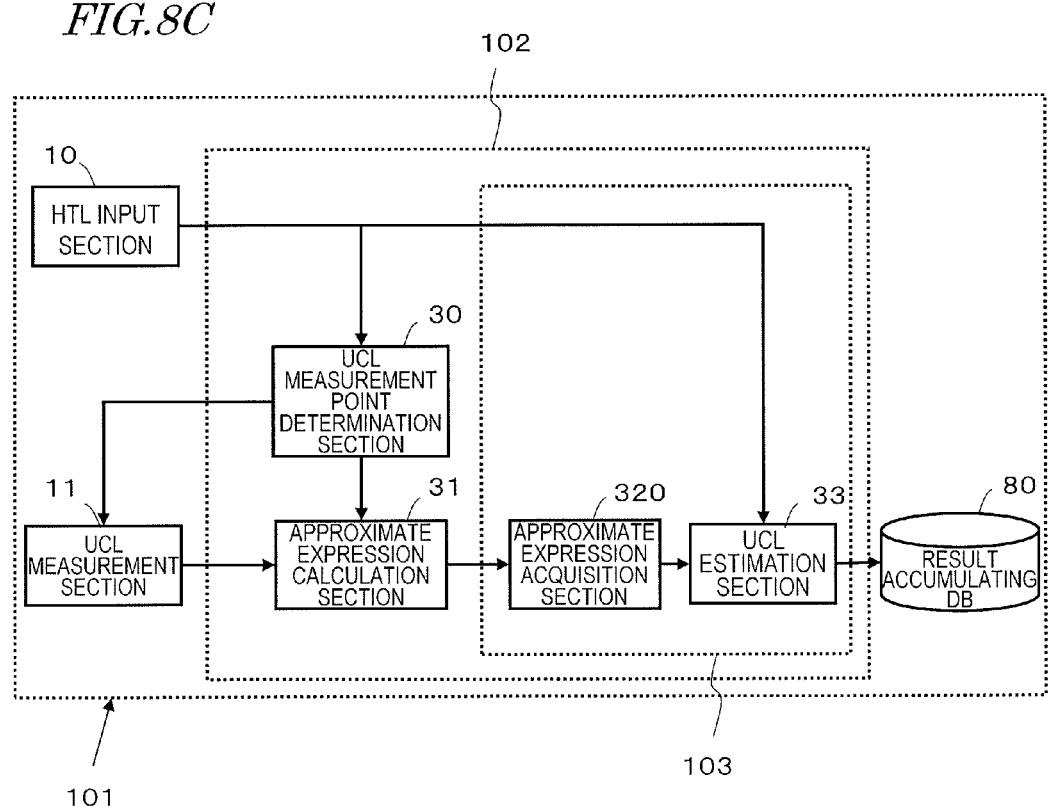
FIG. 8C is a diagram showing the construction of an implementation of an uncomfortable sound pressure estimation system according to Embodiment 1.

FIG. 8C shows a functional block construction of an uncomfortable sound pressure estimation system 101 according to Variant 1 of the present embodiment. The uncomfortable sound pressure estimation system 101 includes an HTL input section 10, a UCL measurement section 11, an uncomfortable sound pressure estimation apparatus 102, and a result accumulating DB 80. Moreover, the uncomfortable sound pressure estimation apparatus 102 includes a UCL measurement point determination section 30, an approximate expression calculation section 31, an approximate expression acquisition section 320, and a UCL estimation section 33. The uncomfortable sound pressure estimation apparatus 102 at least includes an uncomfortable sound pressure estimation processor 103 which includes the approximate expression acquisition section 320 and the UCL estimation section 33. The approximate expression acquisition section 320 acquires predetermined criterions which are associated with different users.

This is identical to the uncomfortable sound pressure estimation system 100 according to Embodiment 1 except for the difference from the approximate expression acquisition section 32. The approximate expression acquisition section 320 acquires the predetermined criterion calculated by the approximate expression calculation section 31, and sends it to the UCL estimation section 33. Unlike the approximate expression acquisition section 32 of Embodiment 1, the approximate expression acquisition section 320 does not make a determination as to whether the approximation coefficients are within predetermined ranges or not. Alternatively, the approximate expression acquisition section 32 may be omitted, and the predetermined criterion calculated by the approximate expression calculation section 31 may directly be sent to the UCL estimation section 33.

Next, with reference to FIG. 11B, a processing procedure of the uncomfortable sound pressure estimation system 101 in FIG. 8C will be described. FIG. 11B is a flowchart showing a procedure of processing by the uncomfortable sound pressure estimation system 101. Since it is substantially similar to the processing in the flowchart of the uncomfortable sound pressure estimation system 100 shown in FIG. 11A except that the processes of step S105 and step S106 are not performed, its description will be kept brief.

<step S101> The HTL input section 10 accepts an HTL of the user for each measurement point. Herein, HTLs are mutually different between at least two measurement points. The HTL input section 10 sends information of the accepted HTLs to the UCL measurement point determination section 30.

<step S102> The UCL measurement point determination section 30 accepts an HTL for each measurement point from the HTL input section 10. From among the accepted HTLs, the UCL measurement point determination section 30 determines at least two measurement points of different HTL values as UCL measurement points, and sends them to the UCL measurement section 11. The UCL measurement point determination section 30 sends the HTLs with respect to the determined measurement points to the approximate expression calculation section 31.

<step S103> The UCL measurement section 11 measures UCL at the measurement points determined by the UCL measurement point determination section 30. It sends the UCL for each measurement point to the approximate expression calculation section 31.

<step S104> By using the HTL for each measurement point as received from the UCL measurement point determination section 30 and the UCLs for the measurement points for which UCLs were actually measured as received from the UCL measurement section 11, the approximate expression calculation section 31 calculates a predetermined criterion concerning HTL and UCL. The predetermined criterion is, for example, information of a proportional relationship between HTL and UCL. Preferably, the predetermined criterion is associated with the user.

<step S107> The UCL estimation section 33 included in the uncomfortable sound pressure estimation processor 103 receives an HTL for each measurement point from the HTL input section 10, and receives the predetermined criterion from the approximate expression calculation section 31. Herein, the predetermined criterion having been output from the approximate expression calculation section 31 is intactly output to the UCL estimation section 33, without being subjected to determination by the approximate expression acquisition section 320 as to being in the predetermined range or not. Although the approximate expression acquisition section 320 is omissible, the approximate expression acquisition section 320 is herein illustrated as a component element of the uncomfortable sound pressure estimation processor 103 which receives the approximate expression from the approximate expression calculation section 31. Against the predetermined criterion, the UCL estimation section 33 estimates a UCL for each received measurement point.

<step S108> The result accumulating DB 80 stores the UCLs received from the UCL estimation section 33 in a measurement point-by-measurement point manner.

Embodiment 2

An uncomfortable sound pressure estimation system 200 according to Embodiment 2 measures UCL of a user with respect to measurement points, from electroencephalographic responses to successive sounds of sound pressures which are generally not felt loud to users. Then, based on UCLs measured from the electroencephalographic responses, an approximate expression is calculated to estimate a UCL at a measurement point for which only HTL was measured but UCL was not measured based on electroencephalograms.

Figure 12:
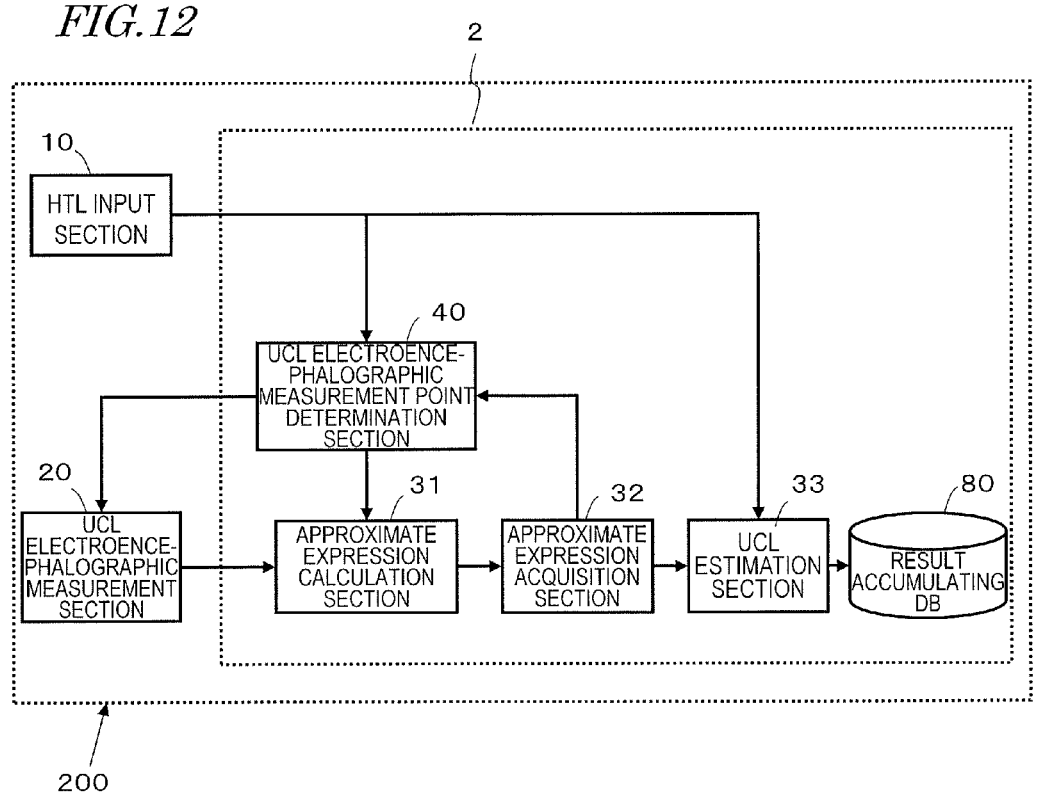
FIG. 12 is a diagram showing the construction of an implementation of an uncomfortable sound pressure estimation system according to Embodiment 2.

FIG. 12 shows a functional block construction of the uncomfortable sound pressure estimation system 200 according to the present embodiment. The uncomfortable sound pressure estimation system 200 includes an HTL input section 10, a UCL electroencephalographic measurement section 20, and an uncomfortable sound pressure estimation apparatus 2. The uncomfortable sound pressure estimation apparatus 2 includes a UCL electroencephalographic measurement point determination section 40, an approximate expression calculation section 31, an approximate expression acquisition section 32, a UCL estimation section 33, and a result accumulating DB 80. The uncomfortable sound pressure estimation apparatus 2 is connected to the HTL input section 10 and the UCL electroencephalographic measurement section 20 in a wired or wireless manner.

Instead of the UCL measurement section 11 in Embodiment 1, the uncomfortable sound pressure estimation system 200 of the present embodiment includes the UCL electroencephalographic measurement section 20. Moreover, the uncomfortable sound pressure estimation apparatus 2 according to the present embodiment differs from the uncomfortable sound pressure estimation apparatus 1 according to Embodiment 1 in that the UCL electroencephalographic measurement point determination section 40 is provided instead of the UCL measurement point determination section 30. Other component elements are similar to those of the uncomfortable sound pressure estimation system 100 of Embodiment 1, and thus are denoted by like reference numerals in FIG. 12, detailed descriptions thereof being omitted.

Hereinafter, the UCL electroencephalographic measurement point determination section 40 and the UCL electroencephalographic measurement section 20 will be described.

<UCL Electroencephalographic Measurement Point Determination Section 40>

Similarly to the UCL measurement point determination section 30 according to Embodiment 1, the UCL electroencephalographic measurement point determination section 40 receives an HTL of the user for each measurement point from the HTL input section 10. Then, it determines measurement points at which the UCL electroencephalographic measurement section 20 measures UCL, and sends them to the UCL electroencephalographic measurement section 20. Moreover, the UCL electroencephalographic measurement point determination section 40 sends HTLs at the determined measurement points to the approximate expression calculation section 31.

In the selection of measurement points for UCL electroencephalographic measurement by the UCL electroencephalographic measurement point determination section 40, the following two criteria are added to the criteria of selection by the UCL measurement point determination section 30 in Example 1. That is, (1) measurement points are to be selected so that the smallest sound pressure among the sound stimulations to be presented during UCL electroencephalographic measurement will be audible. For example, when the smallest sound pressure among the sound stimulations to be presented is 70 dBHL, UCL measurement points are to be selected from among measurement points that are associated with HTLs smaller than 70 dBHL. (2) In order to reduce the influence of taming in electroencephalogram due to repetitive presentation of sound stimulations of the same frequency, measurement points of different frequencies are to be selected.

In addition, the UCL electroencephalographic measurement point determination section 40 receives from the approximate expression acquisition section 32 information as to whether the coefficients of the approximate expression lie outside the predetermined ranges, and if they do, adds two measurement points for UCL electroencephalographic measurement following the aforementioned criteria. While the UCL measurement point determination section 30 according to Example 1 would add one measurement point, it is preferable in order to reduce the influence of taming of electroencephalogram that the UCL electroencephalographic measurement point determination section 40 adds two measurement points of different frequencies.

As is described in Non-Patent Document 2, UCLs which are measured based on electroencephalogram as an index will contain an error of about 5 dB on average. One reason is that correct estimations may not be possible under the influence of noises that are mixed in the electroencephalogram. Therefore, when adding UCL measurement points, the UCL electroencephalographic measurement point determination section 40 may again select the measurement points at which measurement was taken by the UCL electroencephalographic measurement section 20. When such re-selection is made, an arithmetic mean of the event-related potentials may be taken in a manner of continuing on the past results. This improves S/N of the electroencephalogram, and enhances the accuracy of UCL electroencephalographic measurement.

Based on the electroencephalographic responses of the user, the UCL electroencephalographic measurement section 20 measures UCLs at the measurement points determined by the UCL electroencephalographic measurement point determination section 40. It sends the measured UCLs to the approximate expression calculation section 31.

Figure 13:
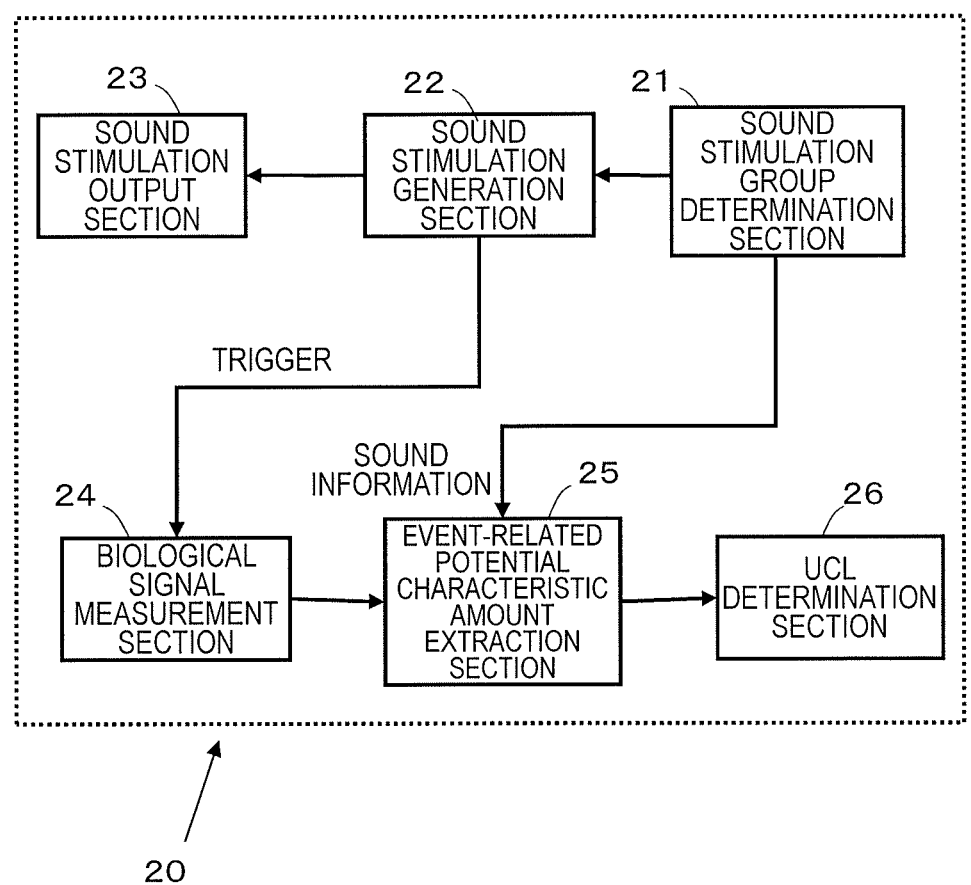
FIG. 13 is a diagram showing a detailed construction of the UCL electroencephalographic estimation section according to Embodiment 2.

FIG. 13 shows a detailed construction of the UCL electroencephalographic measurement section 20. The UCL electroencephalographic measurement section 20 includes a sound stimulation group determination section 21, a sound stimulation generation section 22, a sound stimulation output section 23, a biological signal measurement section 24, an event-related potential characteristic amount extraction section 25, and a UCL determination section 26.

The sound stimulation group determination section 21 receives information of measurement points from the UCL electroencephalographic measurement point determination section 40, and determines information of a plurality of sound stimulations to be presented to the user. The plurality of sound stimulations may also be referred to as a sound stimulation group. The information of the sound stimulation group includes sound pressures of the sound stimulations within the sound stimulation group, durations of sound stimulations within the sound stimulation group, and intervals between plural sound stimulations.

The sound stimulation group may include, for example, a first sound, a second sound, and a third sound to be successively presented as the sound stimulations. Moreover, the first sound, second sound, and third sound may be set so as to consecutively decrease in sound pressure. The sound pressures of the sound stimulations within the sound stimulation group are determined within a sound pressure range smaller than what is generally considered to be UCL, e.g., 80 dBHL, 75 dBHL, 70 dBHL.

The ear to which the sound stimulation group is to be presented and the frequency thereof may be randomly decided under the following constraints, for example. No sound stimulation group of the same frequency as that of an immediately previous sound stimulation group is selected. It is desirable that the right or left ear to which sound stimulations are presented is selected in random order. However, preferably, not more than four sound stimulation groups are successively presented to either the right or left ear alone. Thus, the influence of taming (habituation) of the electroencephalogram due to successive presentation of sound stimulation groups to the same ear and with the same frequency is reduced, whereby UCL determination can be realized with a high precision. The duration of a sound stimulation is set to be e.g. 25 ms or more, so that an auditory evoked potential is stably induced. Moreover, the stimulation interval is set to be an amount of time which is equal to or greater than the duration of a sound stimulation and equal to or less than 1 second. For example, it may be 300 ms, or 200 ms. The sound stimulation group determination section 21 sends the determined sound stimulation information to the sound stimulation generation section 22.

The sound stimulation generation section 22 generates sound stimulation data based on the information of the ear to which the sound stimulation group is to be presented and the frequency thereof, and the durations, stimulation interval, and sound pressures of sound stimulations within the sound stimulation group, which is received from the sound stimulation group determination section 21. Each sound stimulation may be a tone burst sound with a rise and fall of 3 ms, for example.

In accordance with the generated sound stimulation data, the sound stimulation output section 23 outputs sound stimulations to the user. At the timing that the sound stimulations are output, the sound stimulation generation section 22 outputs a trigger signal to the biological signal measurement section 24. Note that the sound stimulation generation section 22 may only send the generated sound stimulation data to the sound stimulation output section 23.

For example, the sound stimulation data may be generated in such a manner that, for one sound stimulation group, only a single piece of sound stimulation data is generated which contains a plurality of sound stimulations that undergo changes in sound pressure at a predetermined time interval. In that case, the trigger signal to be sent to the biological signal measurement section 24 may only be sent at the timing of presenting the first sound.

The sound stimulation output section 23 outputs sound stimulations to the user. The sound stimulation data generated by the sound stimulation generation section 22 is presented to the user as sound stimulations. Preferably, the sound stimulation output section 23 outputs the sound stimulations generated by the sound stimulation generation section 22 to each of the right and left ear as correctly as possible. For example, the sound stimulation output section 23 may be headphones or a loudspeaker having little distortion in the frequency characteristics thereof. The sound stimulation output section 23 may also be referred to as the output section.

The biological signal measurement section 24 is connected to at least two electrodes A and B. For example, electrode A is attached to a mastoid of the user (at a position indicated as Ref in FIG. 16B), whereas electrode B is attached to a central portion (so-called Cz) on the scalp of the user. The biological signal measurement section 24 measures an electroencephalogram of the user that corresponds to a potential difference between electrode A and electrode B. For example, by using electrodes which are worn based on the International 10-20 system shown in FIG. 16A, an electroencephalogram is measured.

Figure 16A:
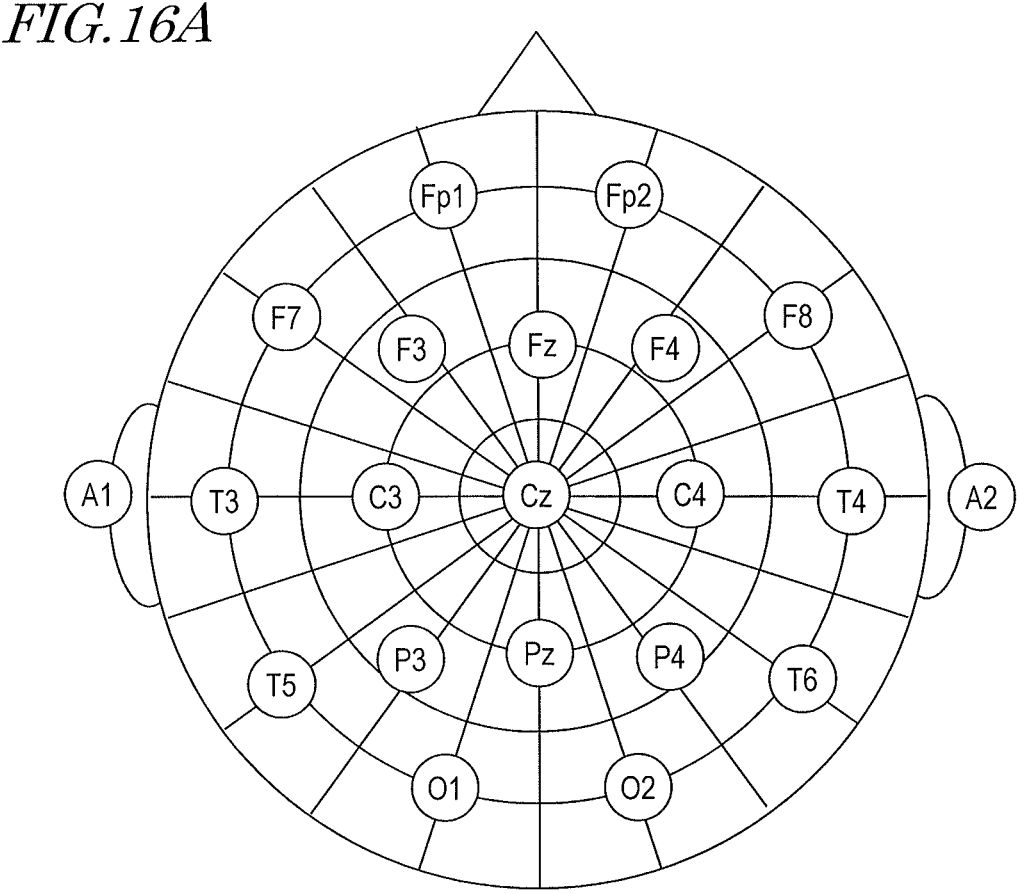
FIG. 16A is a diagram showing electrode positions according to the International 10-20 system.
Figure 16B:
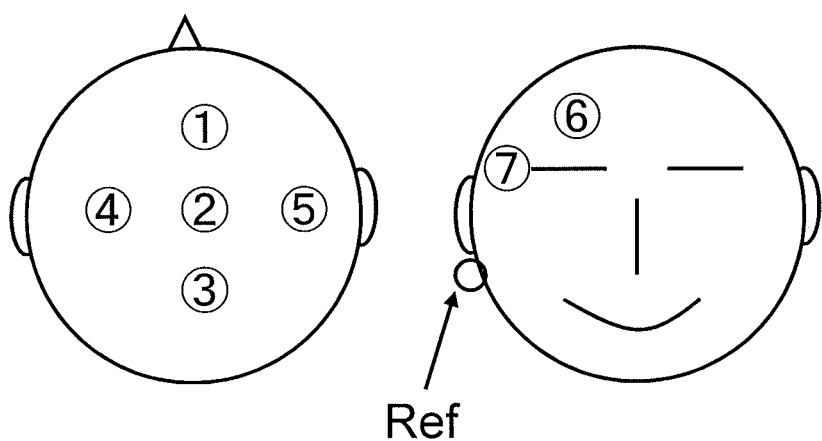
FIG. 16B is a diagram showing electrode positions in an electroencephalographic experiment conducted by the inventors.

Note that the electroencephalographic measurement may be performed with more electrodes. For example, as shown in FIG. 16A, potential differences between active electrodes attached at electrode positions of circled numbers 1 to 5 and a reference electrode attached at the mastoid may be measured as electroencephalograms. Moreover, in order to measure electrooculographic noises that may be mixed in the electroencephalogram due to nictitation and oculomotor movement, electrodes may be placed at positions above the right eye and at the right of the right eye (positions indicated by circled numbers 6 and 7 in FIG. 16B).

The biological signal measurement section 24 is an electroencephalograph which measures a biological signal of the user. The user is supposed to wear at least a probe electrode and a reference electrode. As a biological signal, the biological signal measurement section 24 measures an electroencephalogram corresponding to a potential difference between the probe electrode and the reference electrode. The electroencephalogram data may be subjected to frequency filtering with an appropriate cutoff frequency. The biological signal measurement section 24 sends the measured electroencephalogram or filtered electroencephalogram to the event-related potential characteristic amount extraction section 25. Hereinafter, the measured electroencephalogram or filtered electroencephalogram may also be referred to as electroencephalogram data.

In the case where a band-pass filter is used as the frequency filter, the cutoff frequency may be set so as to pass e.g. 1 Hz to 20 Hz. It is assumed that the user has worn the electroencephalograph in advance.

Based on the electroencephalogram and trigger information received from the biological signal measurement section 24, the event-related potential characteristic amount extraction section 25 cuts out an event-related potential in a predetermined zone based on the trigger information as a starting point (e.g., a zone from 100 ms before presenting the first sound and until 400 ms after presenting the third sound), and in accordance with the particulars of the sound stimulation group received from the sound stimulation group determination section 21, calculates respective wavelet-coefficient related characteristic amounts corresponding to the time-frequency components for the first to third sounds.

A wavelet-coefficient related characteristic amount corresponds to the time-frequency component of an electroencephalographic response (event-related potential) to a sound stimulation. By using this, an uncomfortable sound pressure can be determined. A technique of estimating an uncomfortable sound pressure from a wavelet-coefficient related characteristic amount is disclosed in International Publication No. 2013/057929 by the Applicant. A wavelet-coefficient related characteristic amount is obtained by, for example, applying a continuous wavelet transform to the event-related potential having been cut out, and deriving a wavelet coefficient for each time and for each frequency. As a mother wavelet, for example, the Mexican hat function ($\phi(t)=(1-t^2)\exp(-t^2/2)$) can be used. However, wavelet transform is just one method for determining a time-frequency component of an event-related potential; without being limited to wavelet transform, a time-frequency component may be determined by performing a short-time Fourier transform, for example.

The calculated characteristic amount and information of the sound stimulation group (right or left ear, frequency, sound pressure, etc.) are sent to the UCL determination section 26. The wavelet-coefficient related characteristic amount may be a value obtained through division into predetermined ranges on the frequency axis and on the time axis, and averaging characteristic amounts which are obtained for the respective divided ranges, for example. For example, an average may be taken on the frequency axis based on nine divisions between 2.5 Hz and 125 Hz, and an average may be taken on the time axis based on time ranges of 50 ms. For example, as a P2 component, a biological signal in a time range defined by a latency of 300 ms or less since sound stimulation presentation. The breadth on the frequency axis and on the time axis defining the aforementioned predetermined ranges may be finer or coarser, so long as UCL estimation is possible.

For example, an N1-component event-related potential may be a biological signal which is defined by a negative component in a time range of not less than 50 ms and not more than 150 ms since an auditory stimulation. For example, a P2-component event-related potential may be a biological signal which is defined by a positive component in a time range of not less than 150 ms and not more than 250 ms since an auditory stimulation.

The UCL determination section 26 determines the user's UCL for each measurement point by referring to the characteristic amounts for the first sound, the second sound, and the third sound extracted by the event-related potential characteristic amount extraction section 25, and to a predetermined criterion which previously defines associations between characteristic amounts and UCL values.

Specifically, the UCL determination section 26 determines UCL from the wavelet-coefficient related characteristic amounts for the first to third sounds received from the event-related potential characteristic amount extraction section 25. The UCL determination section 26 performs a linear discrimination by using the previously-provided wavelet characteristic amounts and predetermined criterion.

The predetermined criterion is meant to be information which previously defines associations between characteristic amounts and UCL values. The predetermined criterion may be a table which defines associations between wavelet characteristic amounts and UCLs, or a predetermined equation. The UCL determination section 26 retains the predetermined criterion in advance.

The predetermined criterion is training data for UCL values, for example. The training data is generated from UCLs previously measured through subjective reporting and wavelet characteristic amounts measured through electroencephalogram measurement, of at least two or more other people. The training data may be switched according to the user's symptoms of hypacusia. For example, training data may be prepared and switched between general categories, e.g., conductive deafness and perceptive deafness. Also, training data may be prepared and switched according to the audiogram pattern, e.g., gradual low tone loss or gradual high tone loss. The UCL determination section 26 sends the determined UCLs to the approximate expression calculation section 31.

<Processing by the Uncomfortable Sound Pressure Estimation System 200>

Figure 14:
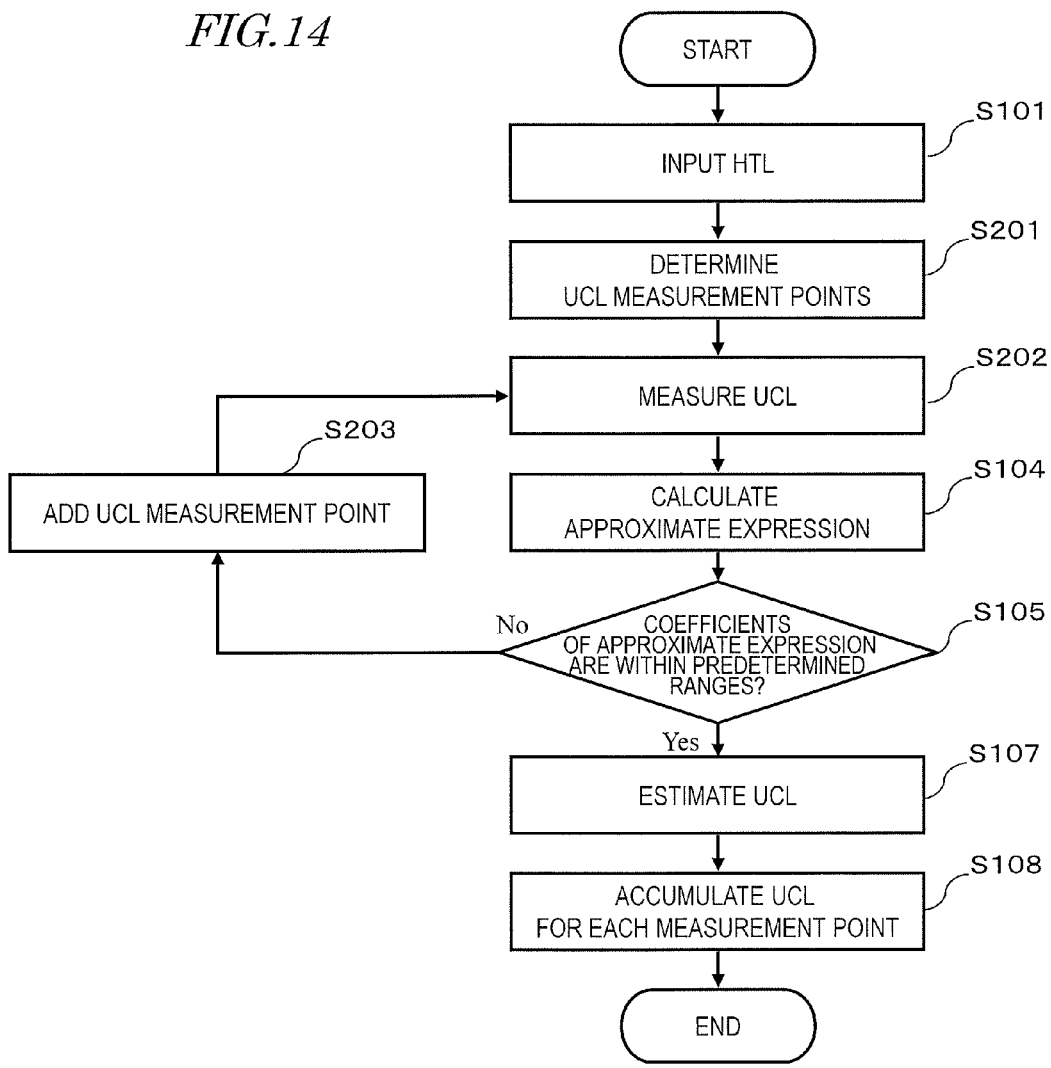
FIG. 14 is a flowchart showing an overall processing by an uncomfortable sound pressure estimation system 200 in outline.

Next, with reference to FIG. 14, a processing procedure performed by the uncomfortable sound pressure estimation system 200 in FIG. 12 will be described. FIG. 14 is a flowchart showing a procedure of processing by the uncomfortable sound pressure estimation system 200. Steps of conducting identical processes to those of the uncomfortable sound pressure estimation system 100 shown in FIG. 11A will be denoted by like reference numerals, and their description will be omitted.

The processing by the uncomfortable sound pressure estimation system 200 according to the present embodiment differs from the uncomfortable sound pressure estimation system 100 according to Embodiment 1 in that steps S201 to S203 related to UCL measurement as indexed by electroencephalographic responses to sound stimulations are included.

At step S201, similarly to the UCL measurement point determination section 30 according to Embodiment 1, the UCL electroencephalographic measurement point determination section 40 receives the user's HTL for each measurement point from the HTL input section 10. Then, measurement points for UCL electroencephalographic measurement by the UCL electroencephalographic measurement section 20 are determined, and sent to the UCL electroencephalographic measurement section 20. Moreover, the UCL electroencephalographic measurement point determination section 40 sends HTLs at the determined measurement points to the approximate expression calculation section 31.

In the selection of measurement points for UCL electroencephalographic measurement by the UCL electroencephalographic measurement point determination section 40, the following two criteria are added to the criteria of selection by the UCL measurement point determination section 30 in Example 1. That is, (1) measurement points are to be selected so that the smallest sound pressure among the sound stimulations to be presented during electroencephalographic measurement will be audible. For example, when the smallest sound pressure among the sound stimulations to be presented is 70 dBHL, measurement points are to be selected so as to result in HTLs smaller than 70 dBHL. (2) In order to reduce the influence of taming in electroencephalogram due to repetitive presentation of sound stimulations of the same frequency, measurement points of different frequencies are to be selected.

At step S202, based on the user's electroencephalographic responses, the UCL electroencephalographic measurement section 20 measures UCLs at the two or more measurement points determined by the UCL electroencephalographic measurement point determination section 40. Then, it sends the measured UCLs to the approximate expression calculation section 31.

At step S105, the approximate expression acquisition section 32 (or more specifically, the approximation coefficient comparison section 321 shown in FIG. 8B) might happen to inform the UCL electroencephalographic measurement point determination section 40 that the coefficients of the approximate expression lie outside the predetermined ranges. In that case, at step S203, the UCL electroencephalographic measurement point determination section 40 adds two or more measurement points of different frequencies as measurement points for UCL electroencephalographic measurement.

With the uncomfortable sound pressure estimation system 200 of the present embodiment, by measuring UCL as indexed by electroencephalographic responses to sound stimulations with respect to at least two measurement points of different HTLs and frequencies, UCLs with respect to other measurement points for which only HTL measurements were taken can be estimated with a high precision. As a result, a hearing aid fitting that does not allow the user to feel loudness during UCL measurement can be easily realized.

Embodiments 1 and 2 are illustrated so that, for each measurement point, the HTL input section 10 accepts an HTL, and the UCL measurement point determination section 30 or the UCL electroencephalographic measurement point determination section 40 determines measurement points at which to actually measure UCLs. However, when there are only two measurement points that led to successful measurement of HTLs, for example, there is no need to determine measurement points. Moreover, for example, for any user whose HTLs are similar between the left ear and the right ear, or any user who wears a hearing aid on only one ear, it suffices if the auditory characteristics of either the right or left ear can be measured. Thus, it is not necessary for the measurement points to include information as to the right ear or left ear, and the measurement points may at least include frequency information.

An uncomfortable sound pressure estimation system according to one embodiment comprises: an HTL acquisition section configured to acquire information of hearing threshold levels respectively for a plurality of frequencies; a UCL measurement point determination section configured to determine at least two measurement points at which to measure uncomfortable sound pressures, each of the at least two measurement points at least defining a first frequency concerning a first hearing threshold level and a second frequency concerning a second hearing threshold level among the acquired hearing threshold levels, the second hearing threshold level being of a different level from the first hearing threshold level; a UCL measurement section configured to measure uncomfortable sound pressures with respect to the at least two determined measurement points; a calculation section configured to calculate a predetermined criterion concerning auditory characteristics by using the respective hearing threshold levels and uncomfortable sound pressures for the at least two measurement points determined by the UCL measurement point determination section; and a UCL estimation section configured to estimate an uncomfortable sound pressure at a frequency corresponding to a given hearing threshold level acquired by the HTL acquisition section, according to the predetermined criterion.

In a system according to one embodiment, by using the respective hearing threshold levels and uncomfortable sound pressures for the at least two measurement points, the calculation section calculates information representing a proportional relationship between the hearing threshold levels and the uncomfortable sound pressures, as the predetermined criterion; and based on the proportional relationship, the UCL estimation section estimates an uncomfortable sound pressure at a measurement point other than the at least two determined measurement points.

In a system according to one embodiment, by using the respective hearing threshold levels and uncomfortable sound pressures for the at least two measurement points, the calculation section calculates an approximate line representing a proportional relationship between the hearing threshold levels and the uncomfortable sound pressures.

A system according to one embodiment further comprises an approximation coefficient comparison section configured to determine whether coefficients concerning a gradient and an intercept of the approximate line are within previously-retained predetermined ranges or not, wherein, when the approximation coefficient comparison section determines that at least one of the gradient and the intercept is out of the predetermined range, the UCL measurement point determination section adds a new measurement point different from the at least two determined measurement points as a measurement point at which to measure the uncomfortable sound pressure; and the calculation section further uses a hearing threshold level and an uncomfortable sound pressure at the new measurement point measured by the UCL measurement section to calculate a proportional relationship between the hearing threshold levels and the uncomfortable sound pressures.

A system according to one embodiment further comprises an approximation coefficient comparison section configured to determine whether coefficients concerning a gradient and an intercept of the approximate line are within previously-retained predetermined ranges or not, wherein, when the approximation coefficient comparison section determines that at least one of the gradient and the intercept is out of the predetermined range, the UCL measurement point determination section again measures uncomfortable sound pressures at the determined measurement points; and the calculation section uses the hearing threshold levels determined by the UCL measurement point determination section and a plurality of uncomfortable sound pressures including the uncomfortable sound pressures again measured by the UCL measurement section to calculate a proportional relationship between the hearing threshold levels and the uncomfortable sound pressures.

In a system according to one embodiment, the predetermined range for gradient is not less than 0.2 and not more than 1, and the predetermined range for intercept is not less than 20 dBSPL and not more than 100 dBSPL.

In a system according to one embodiment, as the at least two measurement points at which to measure uncomfortable sound pressures, the UCL measurement point determination section selects measurement points corresponding to hearing threshold levels associated with frequencies which are not less than 0.9 kHz and not more than 1.1 kHz, among other hearing threshold levels accepted from the HTL acquisition section.

In a system according to one embodiment, as the at least two measurement points at which to measure uncomfortable sound pressures, the UCL measurement point determination section selects a plurality of hearing threshold levels having a predetermined difference or more, among the hearing threshold levels acquired by the HTL acquisition section.

In a system according to one embodiment, as each measurement point, the HTL acquisition section acquires information of a hearing threshold level associated with a left ear or a right ear of a user, in addition to sound frequency; and when a difference between a hearing threshold level for the left ear of the user and a hearing threshold level for the right ear of the user is equal to or greater than a predefined value at the measurement points, the UCL measurement point determination section selects measurement points associated with the ear having a smaller hearing threshold level value as the at least two measurement points at which to measure uncomfortable sound pressures.

In a system according to one embodiment, the UCL measurement section presents a sound stimulation which is equal to or less than a previously-retained predetermined sound pressure, extracts a time-frequency component of an electroencephalographic response to the sound stimulation, and measures an uncomfortable sound pressure by judging from the time-frequency component.

In a system according to one embodiment, from among measurement points resulting in hearing threshold levels equal to or less than a smallest sound pressure among the presented sound stimulations, the UCL measurement point determination section selects the at least two measurement points at which to measure uncomfortable sound pressures.

In a system according to one embodiment, the HTL acquisition section acquires information of a plurality of hearing threshold levels associated with measurement points defined by sound frequency and either a left ear or a right ear of a user, the plurality of hearing threshold levels having different values; and among the accepted hearing threshold levels, the UCL measurement point determination section selects a plurality of hearing threshold levels having different values, and determines measurement points corresponding to the plurality of selected hearing threshold levels as the at least two measurement points at which to measure uncomfortable sound pressures.

An uncomfortable sound pressure estimation processor according to one embodiment is an uncomfortable sound pressure estimation processor to be provided in the above uncomfortable sound pressure estimation system, comprising: an approximate expression acquisition section configured to acquire the information representing a proportional relationship between the hearing threshold levels and the uncomfortable sound pressures calculated by the calculation section; and a UCL estimation section configured to receive information of respective hearing threshold levels for the plurality of frequencies acquired by the HTL acquisition section, and estimating uncomfortable sound pressures corresponding to the hearing threshold levels according to the proportional relationship.

An uncomfortable sound pressure estimation method according to one embodiment comprises the steps of: acquiring information of hearing threshold levels respectively for a plurality of frequencies; determining at least two measurement points at which to measure uncomfortable sound pressures, wherein measurement points respectively associated with at least two hearing threshold levels of different values among the acquired hearing threshold levels are determined as measurement points at which to measure uncomfortable sound pressures; measuring uncomfortable sound pressures with respect to the at least two determined measurement points; calculating a predetermined criterion concerning auditory characteristics by using the respective hearing threshold levels and uncomfortable sound pressures for the at least two measurement points; and estimating an uncomfortable sound pressure at a measurement point other than the at least two measurement points from the acquired hearing threshold levels, according to the predetermined criterion.

A computer program according to one embodiment is a computer program to be executed by a computer mounted in an uncomfortable sound pressure estimation apparatus, the computer program causing the computer to execute the steps of: acquiring information of hearing threshold levels respectively for a plurality of frequencies; determining at least two measurement points at which to measure uncomfortable sound pressures, wherein measurement points respectively associated with at least two hearing threshold levels of different values among the acquired hearing threshold levels are determined as measurement points at which to measure uncomfortable sound pressures; measuring uncomfortable sound pressures with respect to the at least two determined measurement points; calculating a predetermined criterion concerning auditory characteristics by using the respective hearing threshold levels and uncomfortable sound pressures for the at least two measurement points; and estimating an uncomfortable sound pressure at a measurement point other than the at least two measurement points from the acquired hearing threshold levels, according to the predetermined criterion.

An uncomfortable sound pressure estimation system according to one embodiment, comprising one or more memories; and circuitry, which in operation: acquires information of hearing threshold levels respectively for a plurality of frequencies; determines at least two measurement points at which to measure uncomfortable sound pressures, each of the at least two measurement points at least defining a first frequency concerning a first hearing threshold level and a second frequency concerning a second hearing threshold level among the acquired hearing threshold levels, the second hearing threshold level being of a different level from the first hearing threshold level; measures uncomfortable sound pressures with respect to the at least two determined measurement points; calculates a predetermined criterion concerning auditory characteristics by using the respective hearing threshold levels and uncomfortable sound pressures for the at least two determined measurement points; and a UCL estimation section configured to estimate an uncomfortable sound pressure at a frequency corresponding to a given hearing threshold level, according to the predetermined criterion.

In an embodiment of the uncomfortable sound pressure estimation system according to the present disclosure, by taking UCL measurements with respect to at least two measurement points with different HTLs, UCLs with respect to other measurement points for which only HTL measurements were taken can be estimated with a high precision. As a result, the user's trouble in uncomfortable sound pressure estimation is considerably reduced, and a hearing aid fitting is realized that does not allow the user to feel loudness. Also for a person with normal hearing, by estimating his or her uncomfortable sound pressure in advance, applications will become possible such as setting a maximum sound volume for an audio device of a television set or a stereo set.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An uncomfortable sound pressure estimation system, comprising:
   a hearing threshold level (HTL) acquisition section configured to acquire information of hearing threshold levels respectively for a plurality of frequencies;
   a UCL measurement point determination section configured to determine at least two measurement points at which to measure uncomfortable sound pressures, each of the at least two measurement points at least defining a first frequency concerning a first hearing threshold level and a second frequency concerning a second hearing threshold level among the acquired hearing threshold levels, the second hearing threshold level being of a different level from the first hearing threshold level;
   a UCL measurement section configured to measure uncomfortable sound pressures with respect to the at least two determined measurement points;
   a calculation section configured to calculate a predetermined criterion concerning auditory characteristics by using the respective hearing threshold levels and uncomfortable sound pressures for the at least two measurement points determined by the UCL measurement point determination section; and
   an uncomfortable loudness level (UCL) estimation section configured to estimate an uncomfortable sound pressure at a frequency corresponding to a given hearing threshold level acquired by the HTL acquisition section, according to the predetermined criterion.

2. The uncomfortable sound pressure estimation system of claim 1, wherein
   by using the respective hearing threshold levels and uncomfortable sound pressures for the at least two measurement points, the calculation section calculates information representing a proportional relationship between the hearing threshold levels and the uncomfortable sound pressures, as the predetermined criterion; and
   based on the proportional relationship, the UCL estimation section estimates an uncomfortable sound pressure at a measurement point other than the at least two determined measurement points.

3. The uncomfortable sound pressure estimation system of claim 2, wherein, by using the respective hearing threshold levels and uncomfortable sound pressures for the at least two measurement points, the calculation section calculates an approximate line representing a proportional relationship between the hearing threshold levels and the uncomfortable sound pressures.

4. The uncomfortable sound pressure estimation system of claim 3, further comprising an approximation coefficient comparison section configured to determine whether coefficients concerning a gradient and an intercept of the approximate line are within previously-retained predetermined ranges or not, wherein,
   when the approximation coefficient comparison section determines that at least one of the gradient and the intercept is out of the predetermined range, the UCL measurement point determination section adds a new measurement point different from the at least two determined measurement points as a measurement point at which to measure the uncomfortable sound pressure; and
   the calculation section further uses a hearing threshold level and an uncomfortable sound pressure at the new measurement point measured by the UCL measurement section to calculate a proportional relationship between the hearing threshold levels and the uncomfortable sound pressures.

5. The uncomfortable sound pressure estimation system of claim 3, further comprising an approximation coefficient comparison section configured to determine whether coefficients concerning a gradient and an intercept of the approximate line are within previously-retained predetermined ranges or not, wherein,
   when the approximation coefficient comparison section determines that at least one of the gradient and the intercept is out of the predetermined range, the UCL measurement point determination section again measures uncomfortable sound pressures at the determined measurement points; and
   the calculation section uses the hearing threshold levels determined by the UCL measurement point determination section and a plurality of uncomfortable sound pressures including the uncomfortable sound pressures again measured by the UCL measurement section to calculate a proportional relationship between the hearing threshold levels and the uncomfortable sound pressures.

6. The uncomfortable sound pressure estimation system of claim 4, wherein the predetermined range for gradient is not less than 0.2 and not more than 1, and the predetermined range for intercept is not less than 20 dBSPL and not more than 100 dBSPL.

7. The uncomfortable sound pressure estimation system of claim 1, wherein, as the at least two measurement points at which to measure uncomfortable sound pressures, the UCL measurement point determination section selects measurement points corresponding to hearing threshold levels associated with frequencies which are not less than 0.9 kHz and not more than 1.1 kHz, among other hearing threshold levels accepted from the HTL acquisition section.

8. The uncomfortable sound pressure estimation system of claim 1, wherein, as the at least two measurement points at which to measure uncomfortable sound pressures, the UCL measurement point determination section selects a plurality of hearing threshold levels having a predetermined difference or more, among the hearing threshold levels acquired by the HTL acquisition section.

9. The uncomfortable sound pressure estimation system of claim 1, wherein,
   as each measurement point, the HTL acquisition section acquires information of a hearing threshold level associated with a left ear or a right ear of a user, in addition to sound frequency; and
   when a difference between a hearing threshold level for the left ear of the user and a hearing threshold level for the right ear of the user is equal to or greater than a predefined value at the measurement points, the UCL measurement point determination section selects measurement points associated with the ear having a smaller hearing threshold level value as the at least two measurement points at which to measure uncomfortable sound pressures.

10. The uncomfortable sound pressure estimation system of claim 1, wherein the UCL measurement section presents a sound stimulation which is equal to or less than a previously-retained predetermined sound pressure, extracts a time-frequency component of an electroencephalographic response to the sound stimulation, and measures an uncomfortable sound pressure by judging from the time-frequency component.

11. The uncomfortable sound pressure estimation system of claim 10, wherein, from among measurement points resulting in hearing threshold levels equal to or less than a smallest sound pressure among the presented sound stimulations, the UCL measurement point determination section selects the at least two measurement points at which to measure uncomfortable sound pressures.

12. The uncomfortable sound pressure estimation system of claim 1, wherein,
the HTL acquisition section acquires information of a plurality of hearing threshold levels associated with measurement points defined by sound frequency and either a left ear or a right ear of a user, the plurality of hearing threshold levels having different values; and
among the accepted hearing threshold levels, the UCL measurement point determination section selects a plurality of hearing threshold levels having different values, and determines measurement points corresponding to the plurality of selected hearing threshold levels as the at least two measurement points at which to measure uncomfortable sound pressures.

13. An uncomfortable sound pressure estimation processor to be provided in the uncomfortable sound pressure estimation system of claim 2, comprising:
an approximate expression acquisition section configured to acquire the information representing a proportional relationship between the hearing threshold levels and the uncomfortable sound pressures calculated by the calculation section; and
a UCL estimation section configured to receive information of respective hearing threshold levels for the plurality of frequencies acquired by the HTL acquisition section, and estimating uncomfortable sound pressures corresponding to the hearing threshold levels according to the proportional relationship.

14. An uncomfortable sound pressure estimation method comprising the steps of:
acquiring information of hearing threshold levels respectively for a plurality of frequencies;
determining at least two measurement points at which to measure uncomfortable sound pressures, wherein measurement points respectively associated with at least two hearing threshold levels of different values among the acquired hearing threshold levels are determined as measurement points at which to measure uncomfortable sound pressures;
measuring uncomfortable sound pressures with respect to the at least two determined measurement points;
calculating a predetermined criterion concerning auditory characteristics by using the respective hearing threshold levels and uncomfortable sound pressures for the at least two measurement points; and
estimating an uncomfortable sound pressure at a measurement point other than the at least two measurement points from the acquired hearing threshold levels, according to the predetermined criterion,
wherein at least one of the acquiring, the determining, the measuring, the calculating and the estimating is performed by circuitry.

15. The uncomfortable sound pressure estimation system of claim 5, wherein the predetermined range for gradient is not less than 0.2 and not more than 1, and the predetermined range for intercept is not less than 20 dBSPL and not more than 100 dBSPL.

16. An uncomfortable sound pressure estimation system, comprising one or more memories; and circuitry, which in operation:
acquires information of hearing threshold levels respectively for a plurality of frequencies;
determines at least two measurement points at which to measure uncomfortable sound pressures, each of the at least two measurement points at least defining a first frequency concerning a first hearing threshold level and a second frequency concerning a second hearing threshold level among the acquired hearing threshold levels, the second hearing threshold level being of a different level from the first hearing threshold level;
measures uncomfortable sound pressures with respect to the at least two determined measurement points;
calculates a predetermined criterion concerning auditory characteristics by using the respective hearing threshold levels and uncomfortable sound pressures for the at least two determined measurement points; and
an uncomfortable loudness level (UCL) estimation section configured to estimate an uncomfortable sound pressure at a frequency corresponding to a given hearing threshold level, according to the predetermined criterion.

* * * * *